(12) United States Patent
Saladin et al.

(10) Patent No.: US 9,402,655 B2
(45) Date of Patent: Aug. 2, 2016

(54) INTERSPINOUS SPACER ASSEMBLY

(75) Inventors: Stefan Saladin, Oltingen (CH); Felix Aschmann, Basel (CH); Manuel Schaer, Muttenz (CH); Justin Coppes, Downingtown, PA (US); Nicholas Angert, Paoli, PA (US); Grant Skidmore, Virginia Beach, VA (US); Michael Mayer, Graefelfing (DE)

(73) Assignee: DePuy Synthes Products, Inc., Raynham, MA (US)

( * ) Notice: Subject to any disclaimer, the term of this patent is extended or adjusted under 35 U.S.C. 154(b) by 128 days.

(21) Appl. No.: 13/058,553

(22) PCT Filed: Aug. 13, 2009

(86) PCT No.: PCT/US2009/053727
§ 371 (c)(1),
(2), (4) Date: Feb. 11, 2011

(87) PCT Pub. No.: WO2010/019783
PCT Pub. Date: Feb. 18, 2010

(65) Prior Publication Data
US 2011/0144692 A1 Jun. 16, 2011

Related U.S. Application Data

(60) Provisional application No. 61/088,574, filed on Aug. 13, 2008.

(51) Int. Cl.
*A61B 17/70* (2006.01)
*A61B 17/02* (2006.01)
*A61B 17/86* (2006.01)

(52) U.S. Cl.
CPC ......... *A61B 17/7065* (2013.01); *A61B 17/7053* (2013.01); *A61B 17/7068* (2013.01);

(Continued)

(58) Field of Classification Search
CPC ........... A61B 17/7065; A61B 17/7067; A61B 17/7068
USPC .................................................. 606/246–279
See application file for complete search history.

(56) References Cited

U.S. PATENT DOCUMENTS 6,099,527 A 8/2000 Hochschuler et al.
7,048,736 B2 5/2006 Robinson et al.
(Continued)

FOREIGN PATENT DOCUMENTS

CN 101217917 7/2008
EP 2016915 B1 6/2010
(Continued)

OTHER PUBLICATIONS

International Search Report and Written Opinion, dated Mar. 19, 2010, received from the European Patent Office in connection with International Application No. PCT/US2009/053727.

(Continued)

*Primary Examiner* — Nicholas Plionis
(74) *Attorney, Agent, or Firm* — Meunier Carlin & Curfman LLC

(57) ABSTRACT

An interspinous spacer assembly (100) for insertion and/or implantation between spinous processes of adjacent superior and inferior vertebrae includes an interspinous spacer member (110) sized and configured for insertion into the interspinous space located between adjacent spinous processes and an engagement mechanism (105) for operatively coupling the spacer member to the adjacent spinous processes and for preventing migration of the assembly once implanted. The interspinous spacer assembly is adjustable to conform to the individual anatomy of a patient's spine.

19 Claims, 25 Drawing Sheets

(52) U.S. Cl.
CPC .......... *A61B17/8665* (2013.01); *A61B 17/025* (2013.01); *A61B 17/7052* (2013.01); *A61B 17/8605* (2013.01); *A61B 17/8695* (2013.01)

(56) References Cited

U.S. PATENT DOCUMENTS

| | | | |
|---|---|---|---|
| 7,727,233 B2 | 6/2010 | Blackwell et al. | |
| 7,763,073 B2 | 7/2010 | Hawkins et al. | |
| 7,871,426 B2 | 1/2011 | Chin et al. | |
| 8,226,653 B2 | 7/2012 | Blackwell et al. | |
| 8,241,330 B2 | 8/2012 | Lamborne et al. | |
| 8,382,801 B2 | 2/2013 | Lamborne et al. | |
| 8,679,161 B2 | 3/2014 | Malandain et al. | |
| 2002/0029039 A1* | 3/2002 | Zucherman et al. | 606/61 |
| 2003/0040746 A1 | 2/2003 | Mitchell | |
| 2005/0203512 A1 | 9/2005 | Hawkins et al. | |
| 2005/0228377 A1* | 10/2005 | Chao et al. | 606/61 |
| 2006/0241601 A1* | 10/2006 | Trautwein et al. | 606/61 |
| 2006/0247640 A1* | 11/2006 | Blackwell et al. | 606/71 |
| 2007/0072475 A1* | 3/2007 | Justin et al. | 439/354 |
| 2008/0140125 A1 | 6/2008 | Mitchell | |
| 2008/0161818 A1 | 7/2008 | Kloss et al. | |
| 2008/0183211 A1 | 7/2008 | Lamborne et al. | |
| 2008/0234824 A1* | 9/2008 | Youssef et al. | 623/17.16 |
| 2009/0264927 A1 | 10/2009 | Ginsberg et al. | |
| 2009/0326581 A1 | 12/2009 | Galley et al. | |
| 2010/0036419 A1 | 2/2010 | Patel et al. | |
| 2010/0087860 A1 | 4/2010 | Chin et al. | |
| 2010/0152775 A1 | 6/2010 | Seifert et al. | |
| 2010/0211101 A1 | 8/2010 | Blackwell et al. | |
| 2010/0241167 A1 | 9/2010 | Taber et al. | |
| 2010/0318127 A1 | 12/2010 | Phan et al. | |
| 2011/0022090 A1 | 1/2011 | Gordon et al. | |
| 2011/0029020 A1 | 2/2011 | Gordon et al. | |
| 2011/0112577 A1 | 5/2011 | Zucherman et al. | |
| 2011/0172711 A1 | 7/2011 | Kirschman | |
| 2011/0319936 A1 | 12/2011 | Gordon et al. | |
| 2012/0089184 A1 | 4/2012 | Yeh | |
| 2012/0109203 A1 | 5/2012 | Dryer | |
| 2012/0221051 A1 | 8/2012 | Robinson | |
| 2012/0239089 A1 | 9/2012 | Druma et al. | |
| 2012/0323276 A1 | 12/2012 | Okamoto | |
| 2013/0158604 A1 | 6/2013 | Okamoto | |
| 2013/0184752 A1 | 7/2013 | Binder | |
| 2013/0331890 A1 | 12/2013 | Calvosa et al. | |
| 2014/0094848 A1 | 4/2014 | Robinson | |
| 2014/0114355 A1 | 4/2014 | Robinson | |
| 2014/0188170 A1 | 7/2014 | Zappacosta et al. | |

FOREIGN PATENT DOCUMENTS

| | | |
|---|---|---|
| WO | 2005041792 A | 5/2005 |
| WO | 2006084444 A | 8/2006 |

OTHER PUBLICATIONS

Amended claims in EP Application No. 06705937.8 filed in European Patent Office on Apr. 8, 2011 (corresponding to U.S. Appl. No. 11/815,757, U.S. Pat. No. US2008/0161818, published Jul. 3, 2008 to Kloss et al.

* cited by examiner

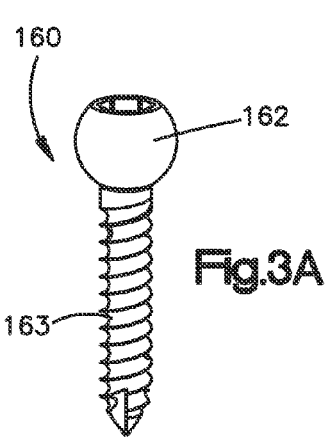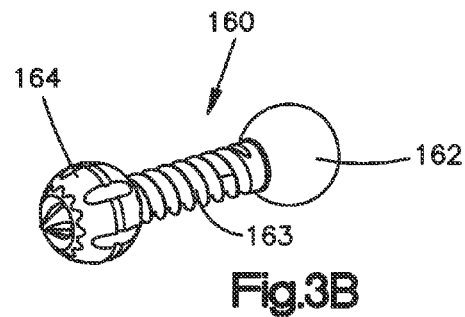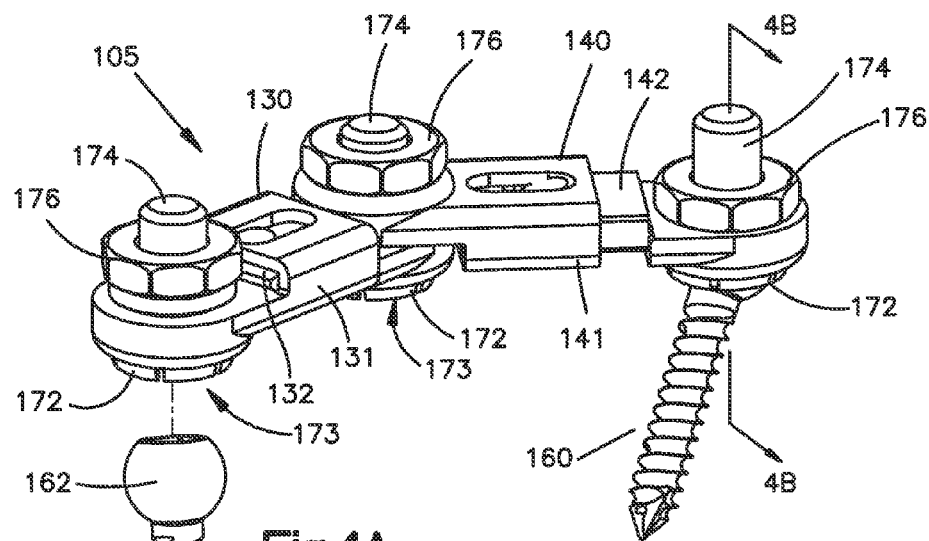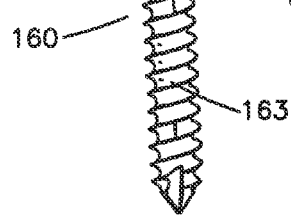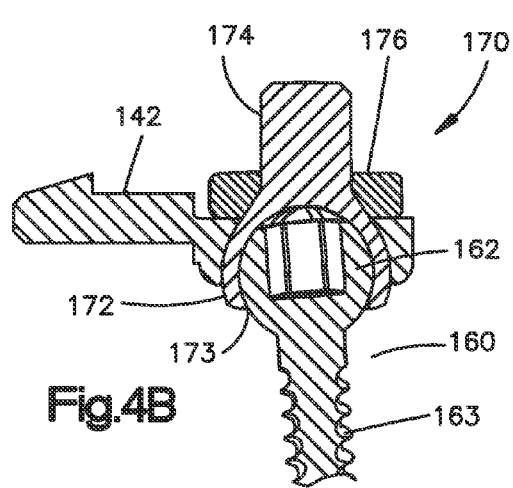

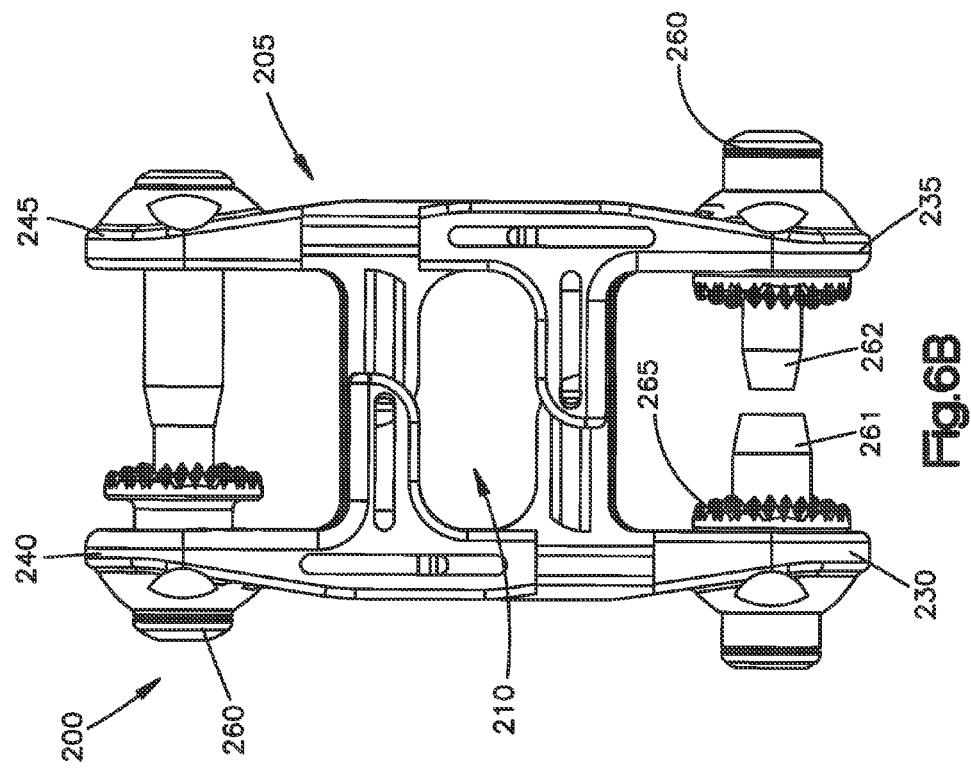
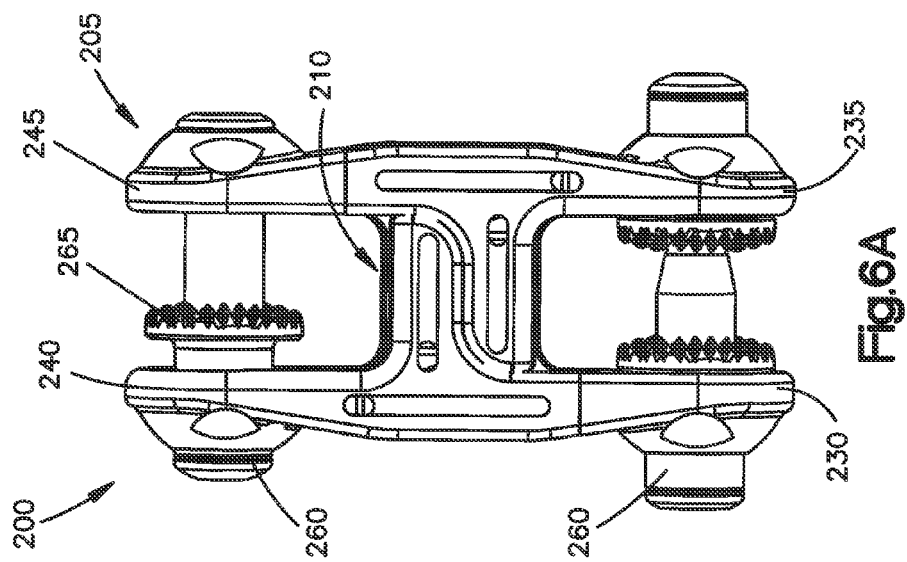

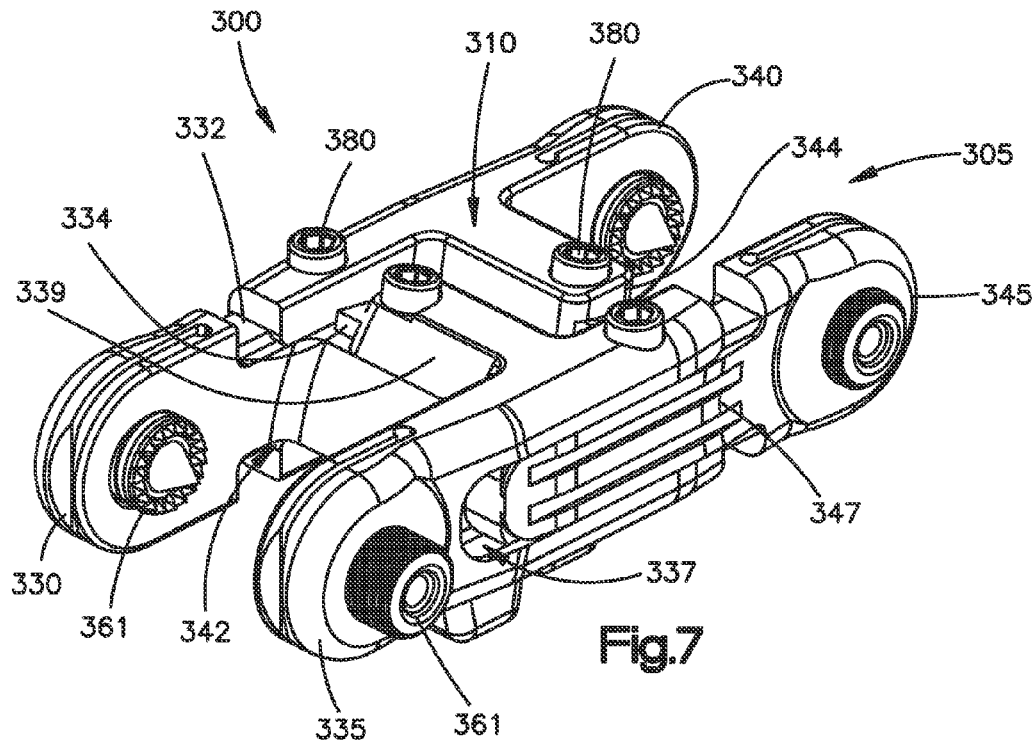
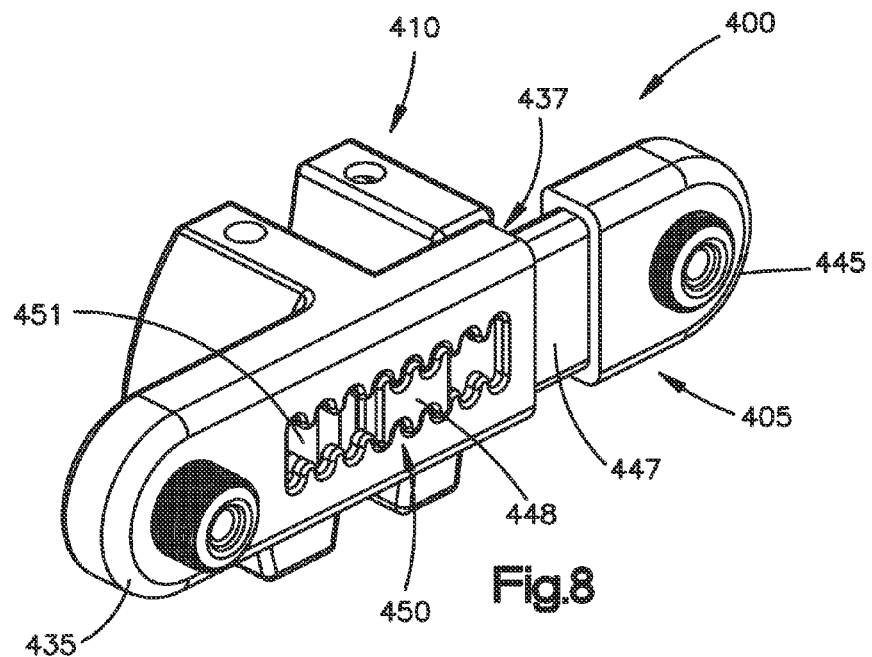

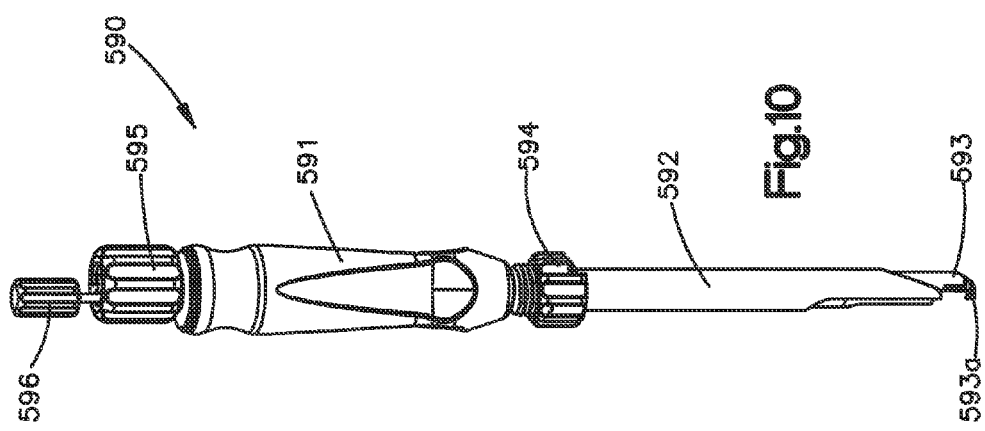
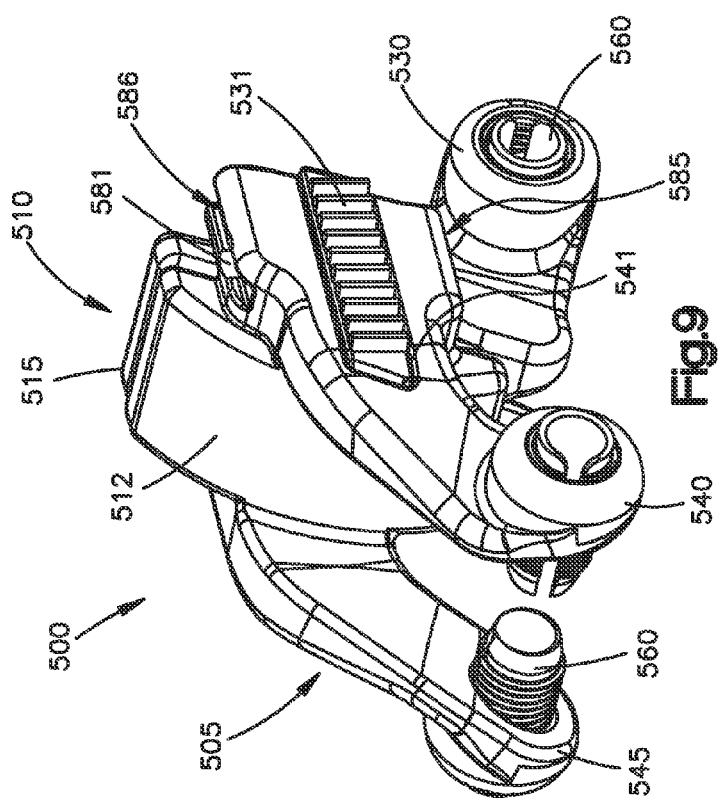

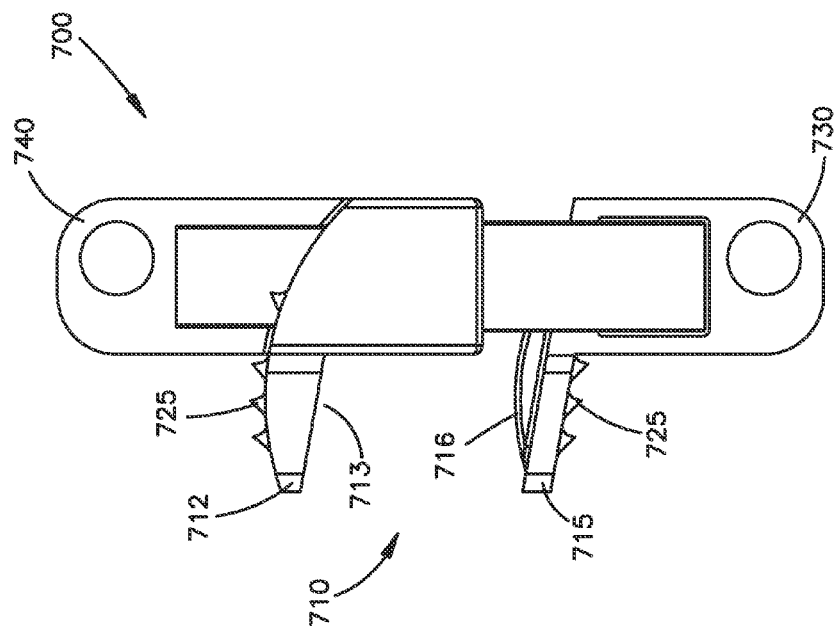
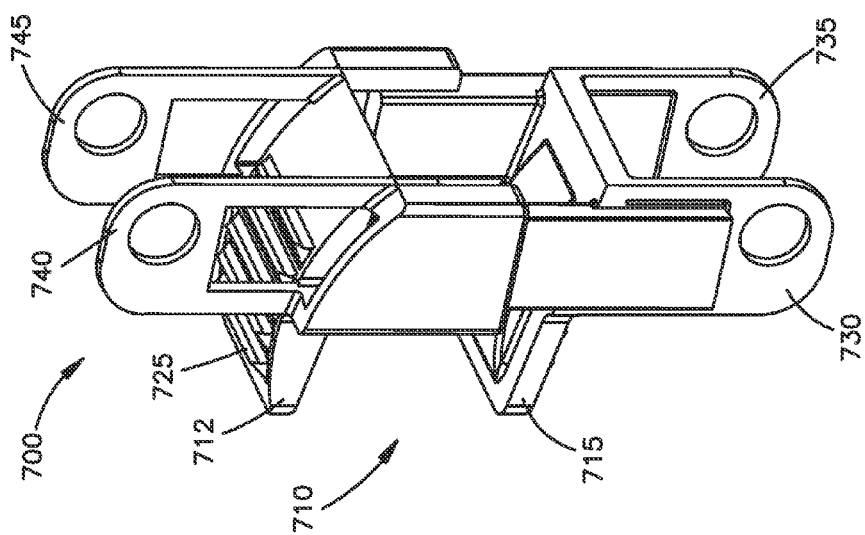

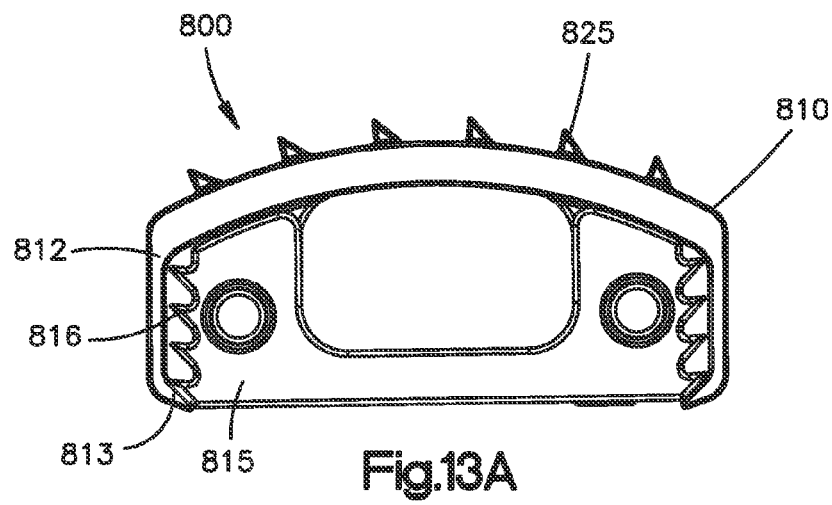
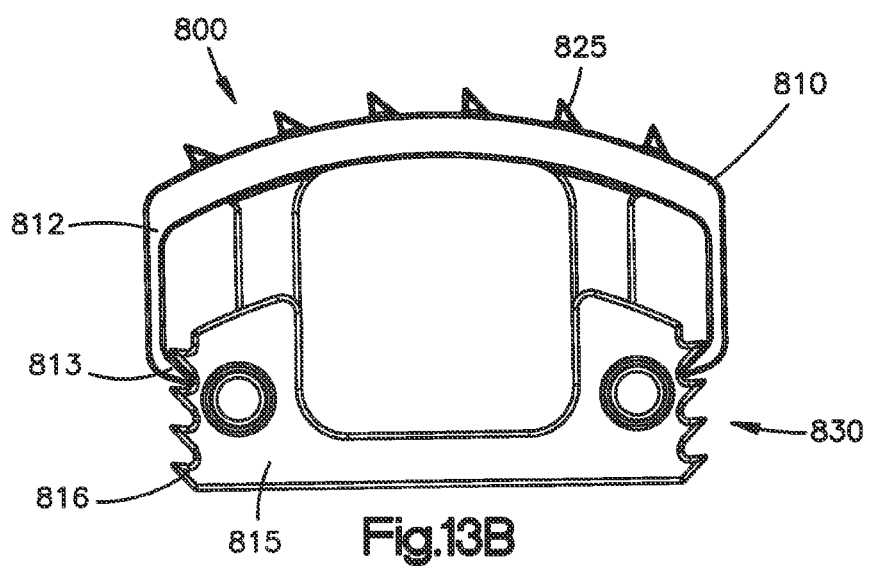
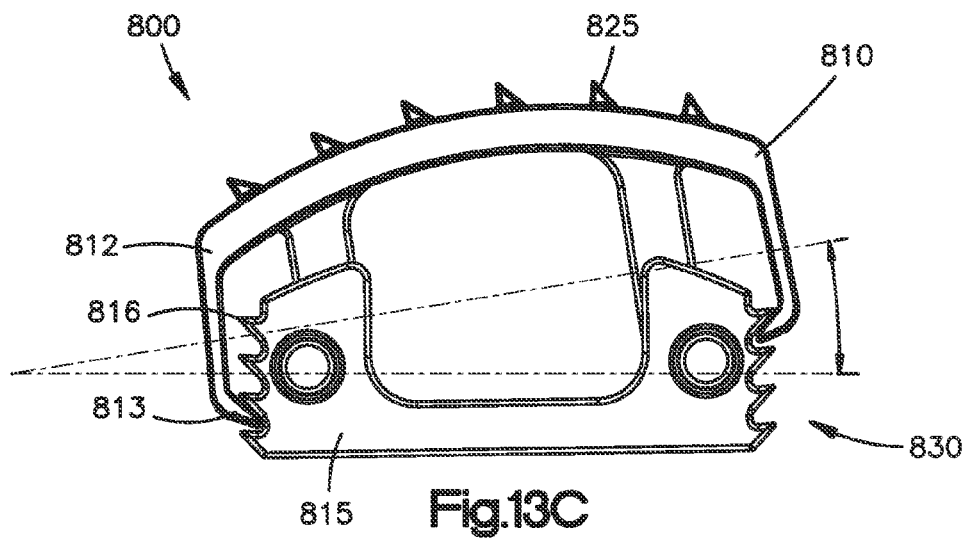

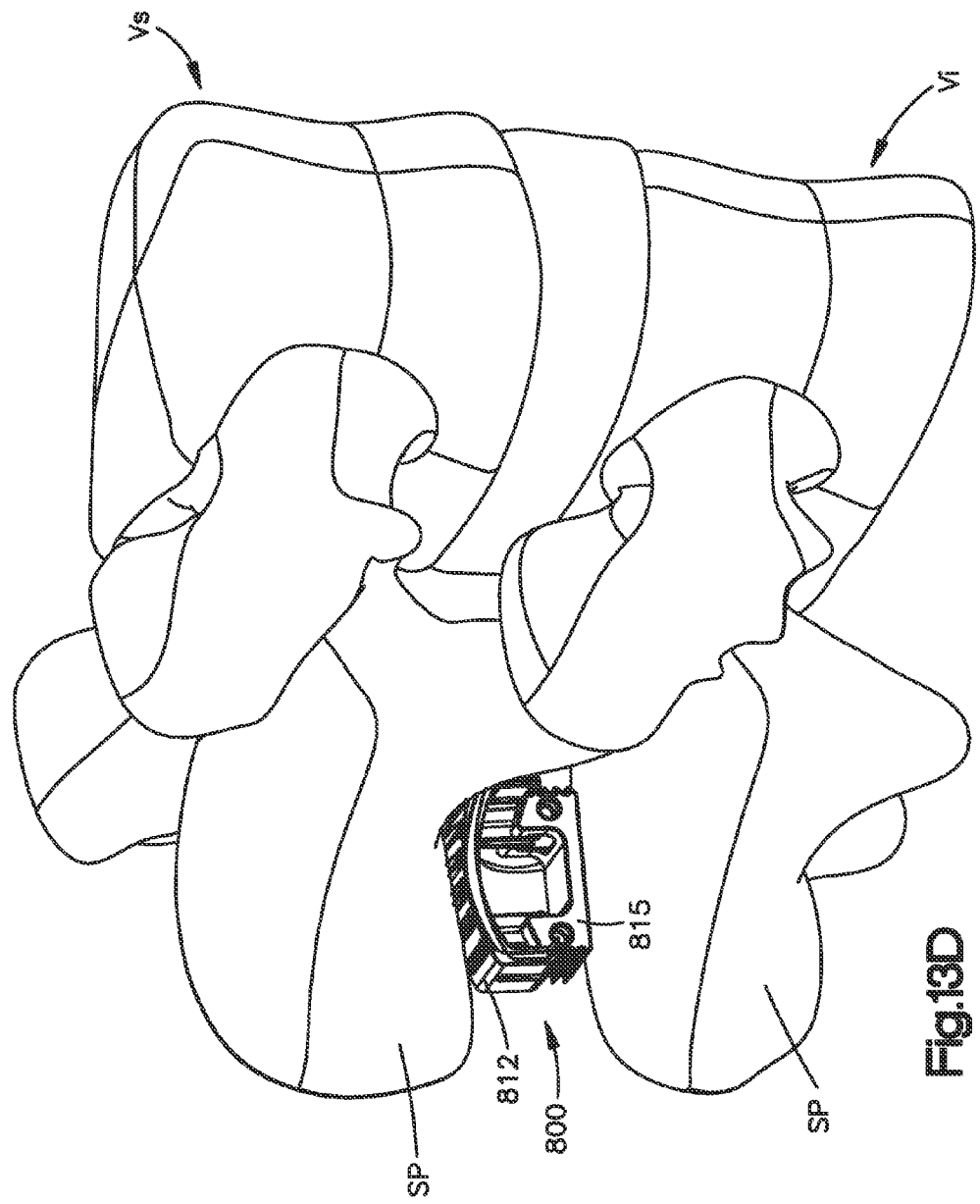

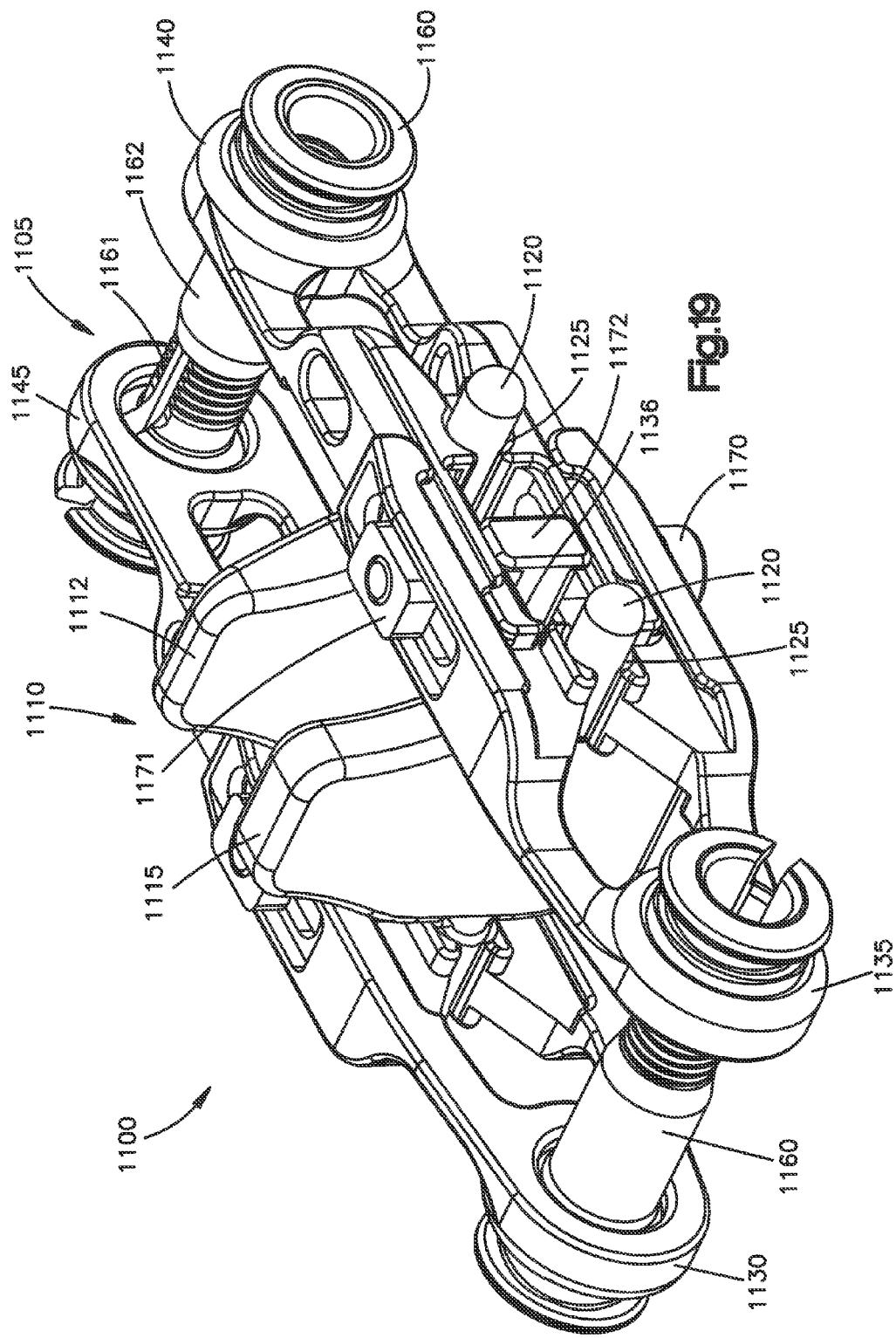

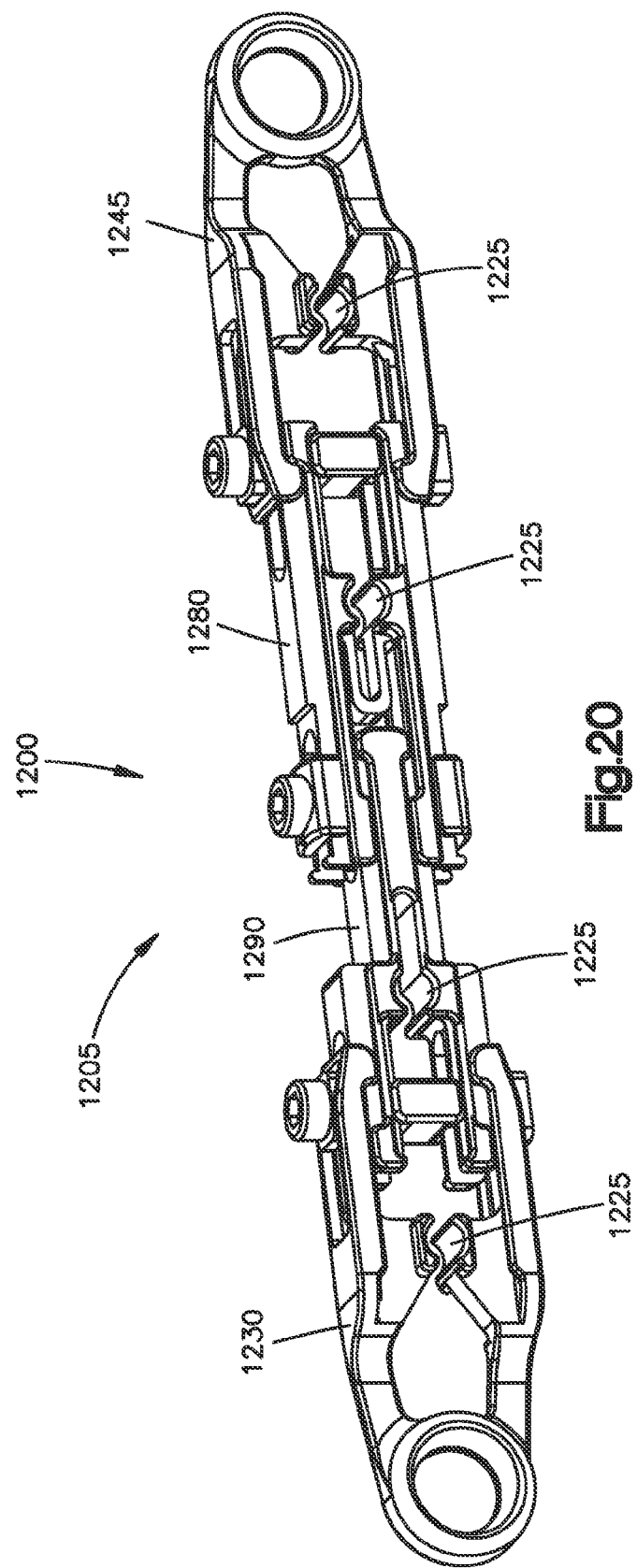

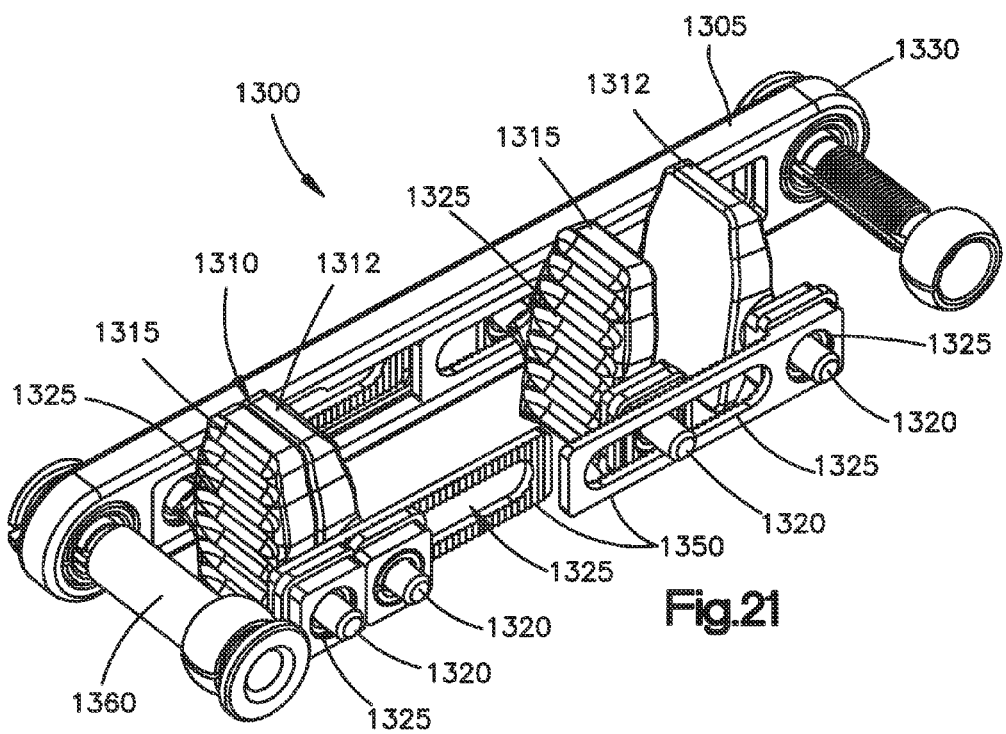
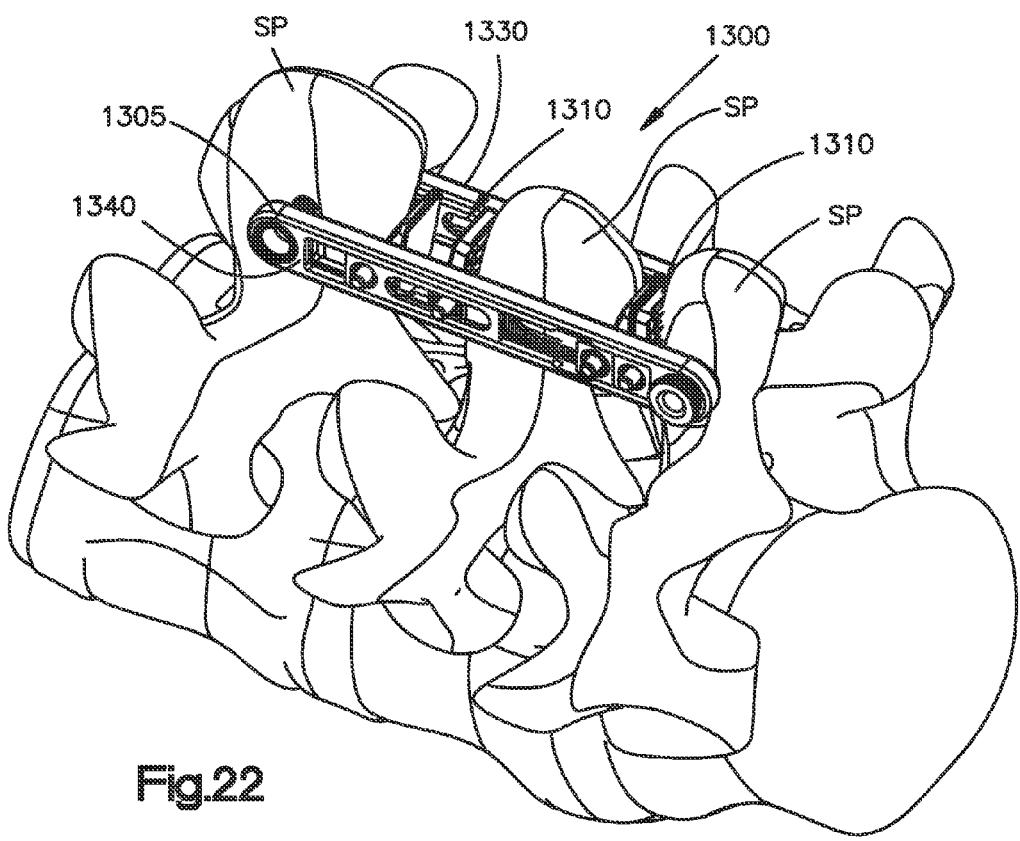

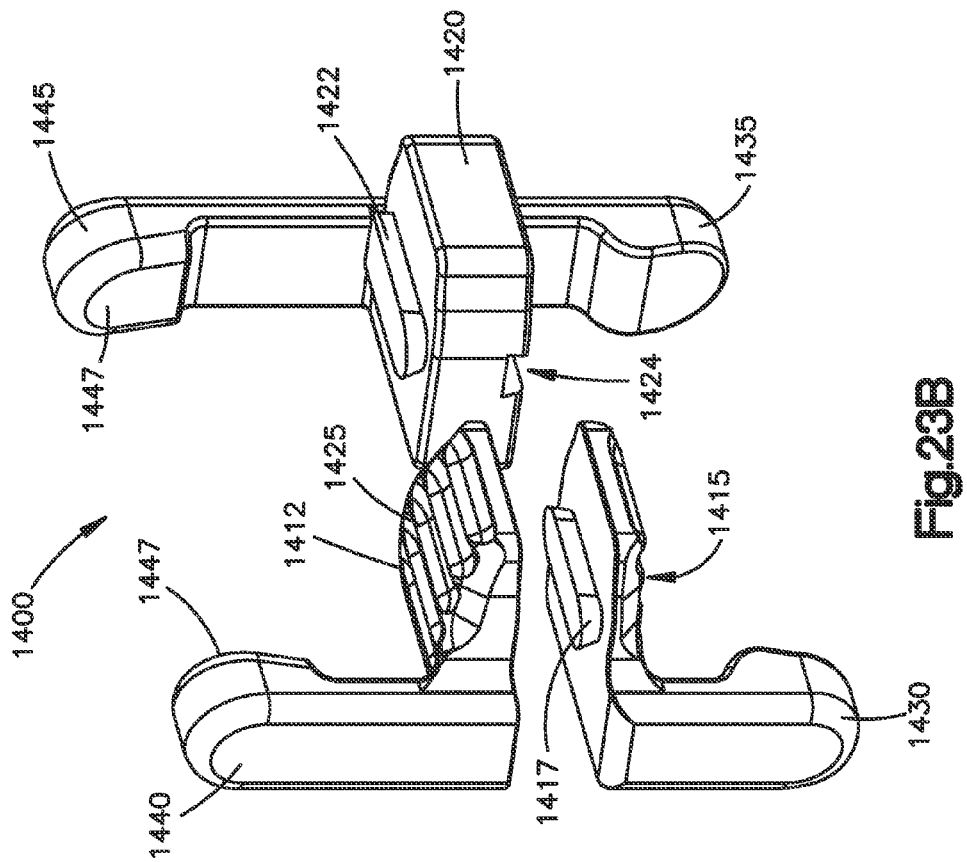
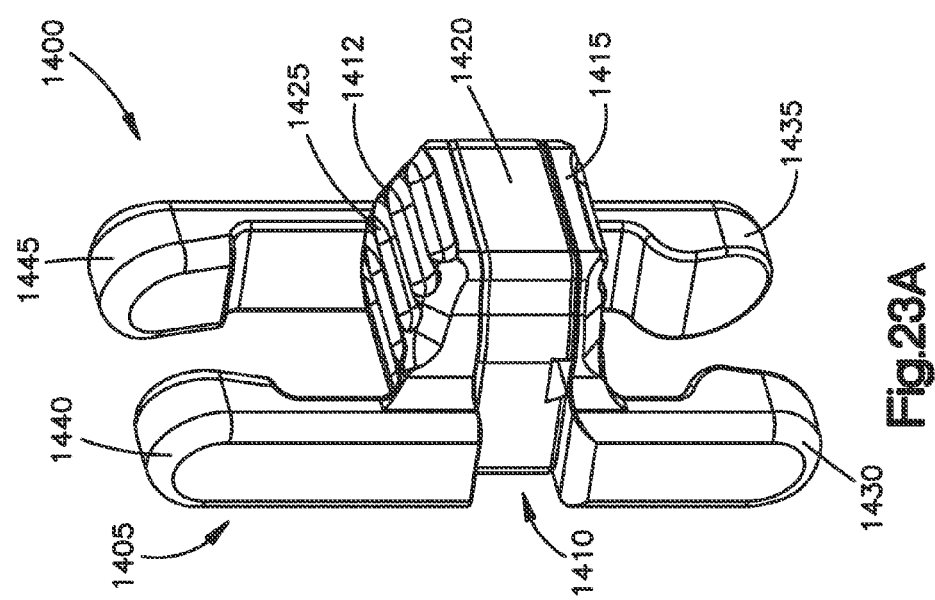

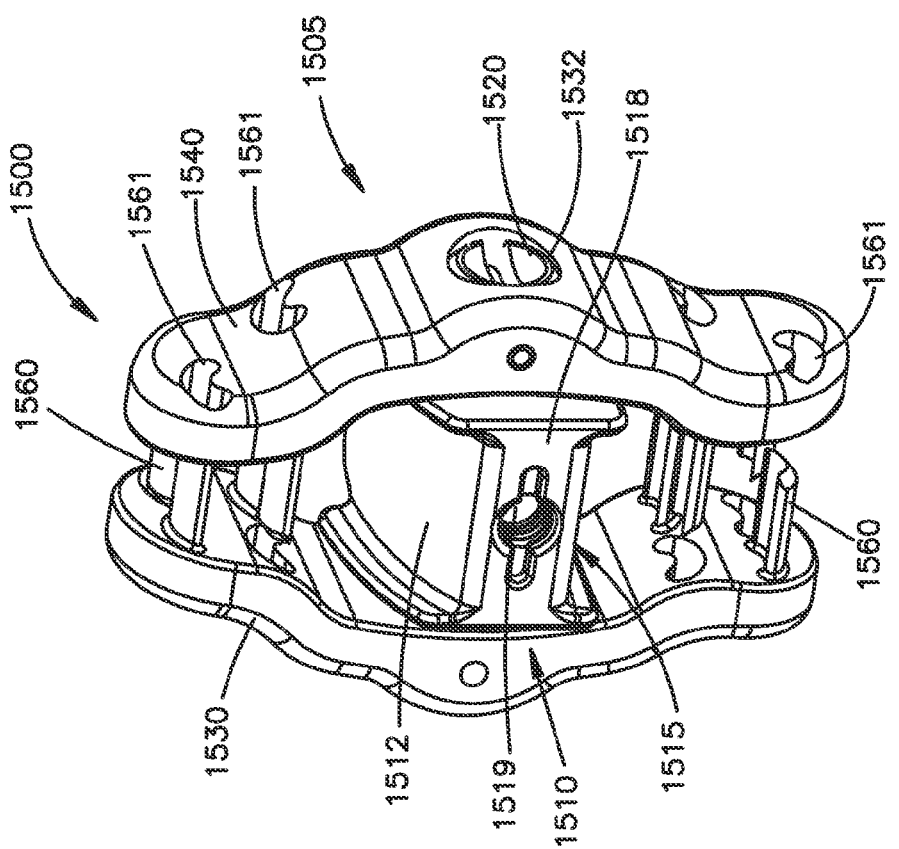
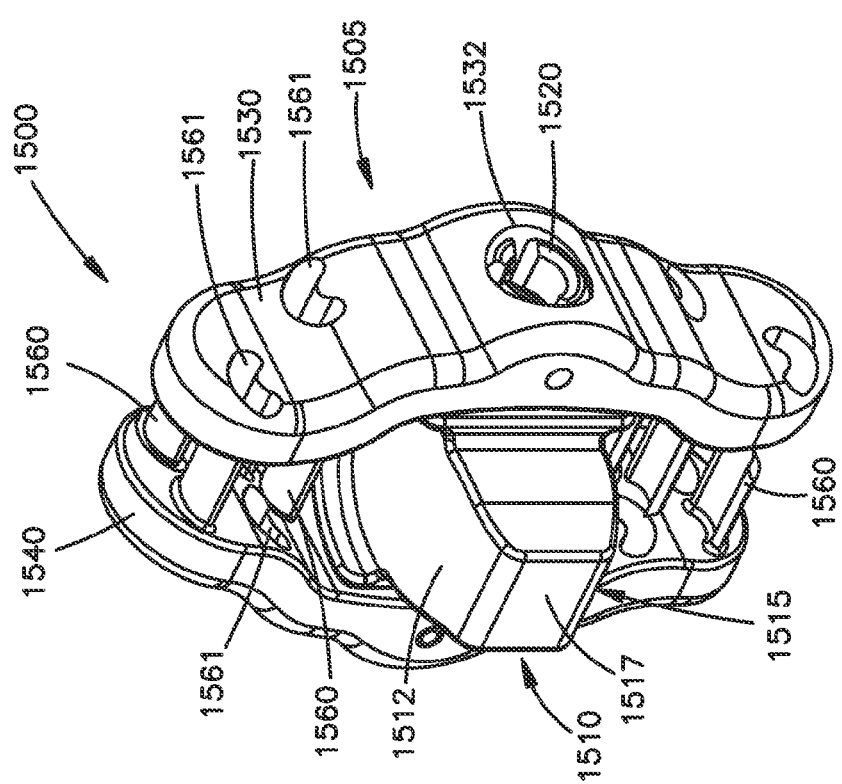

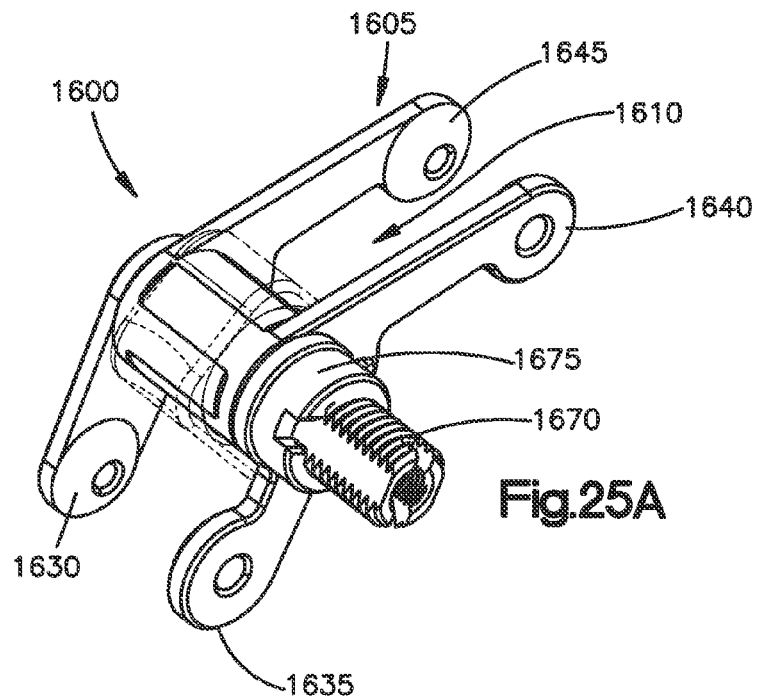
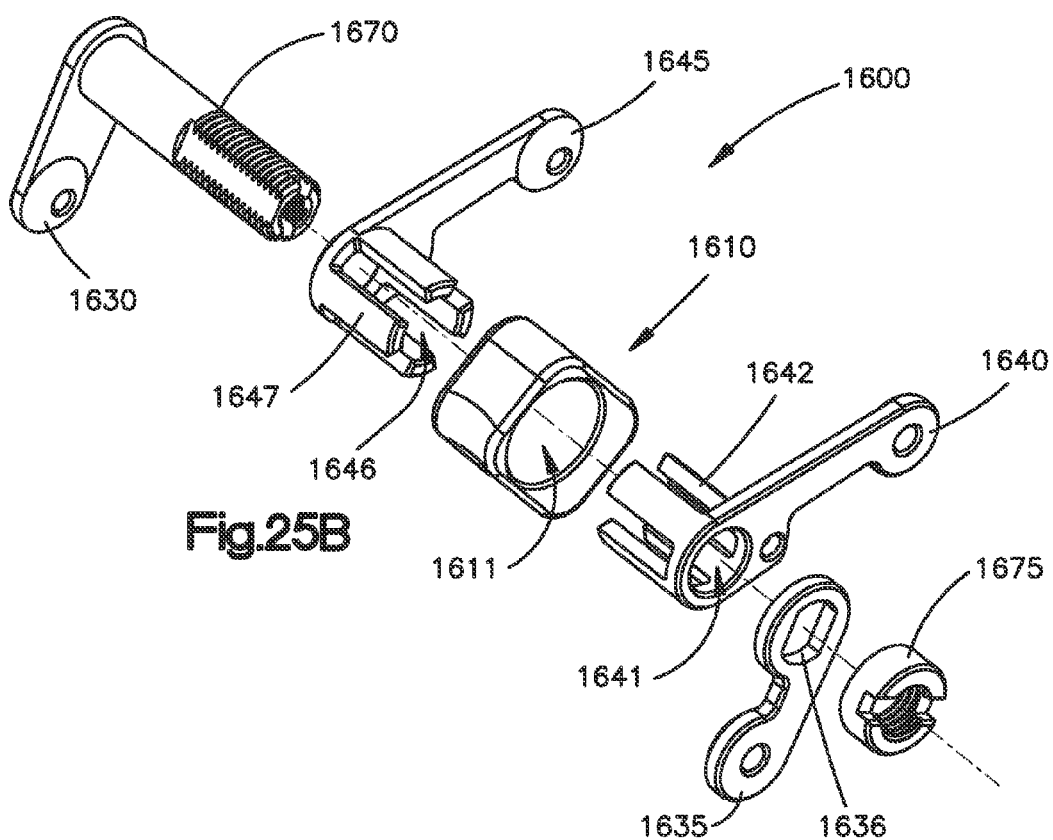

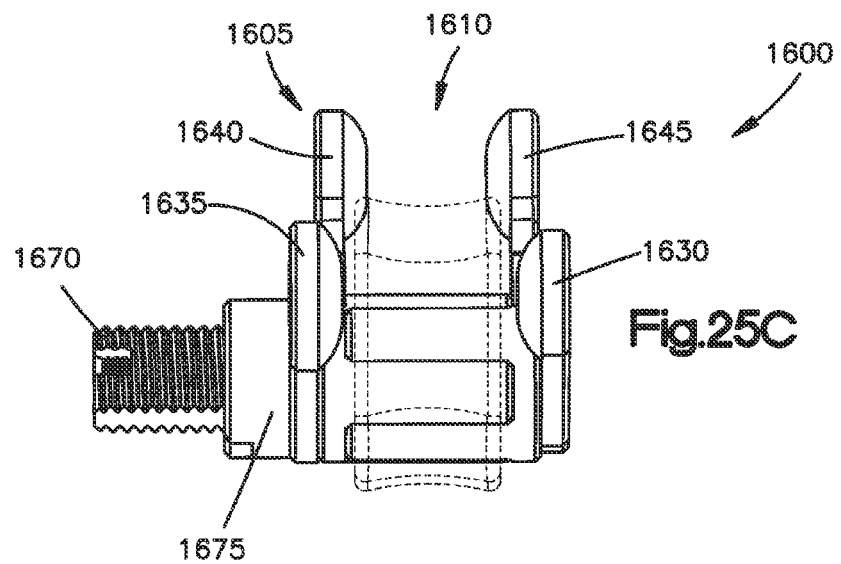
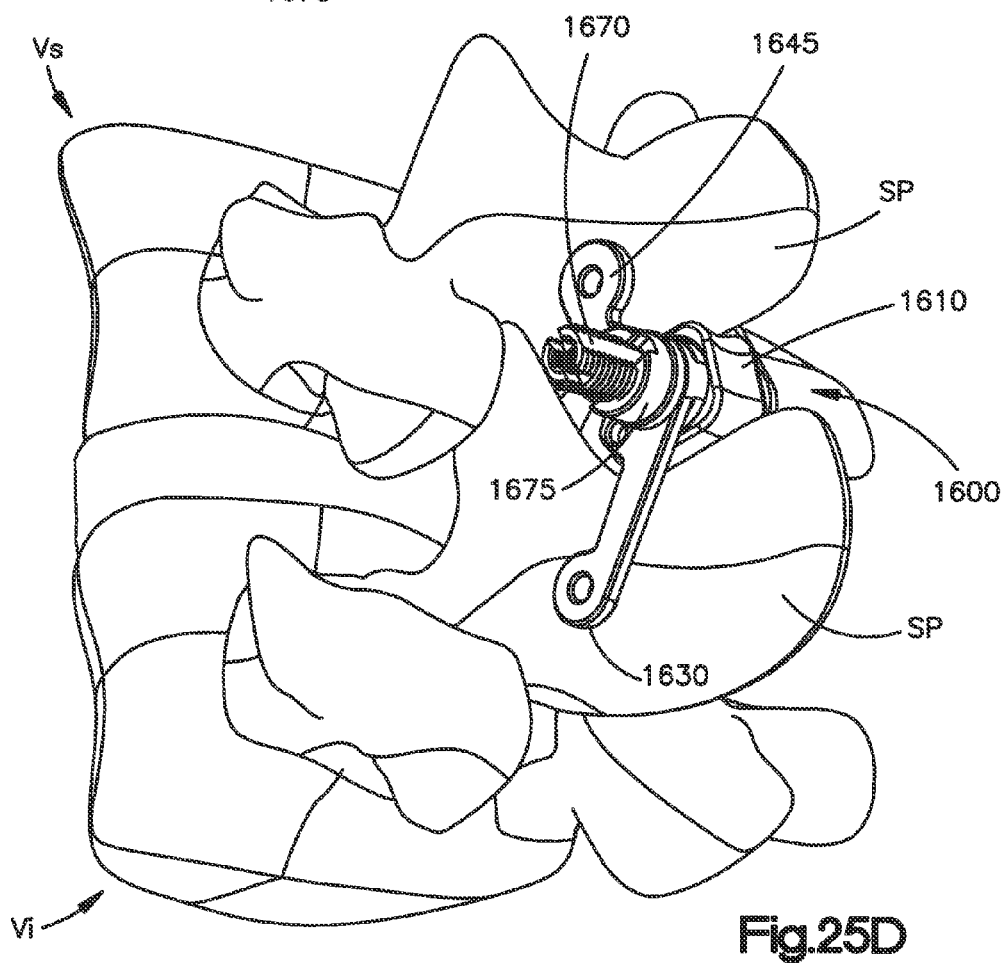

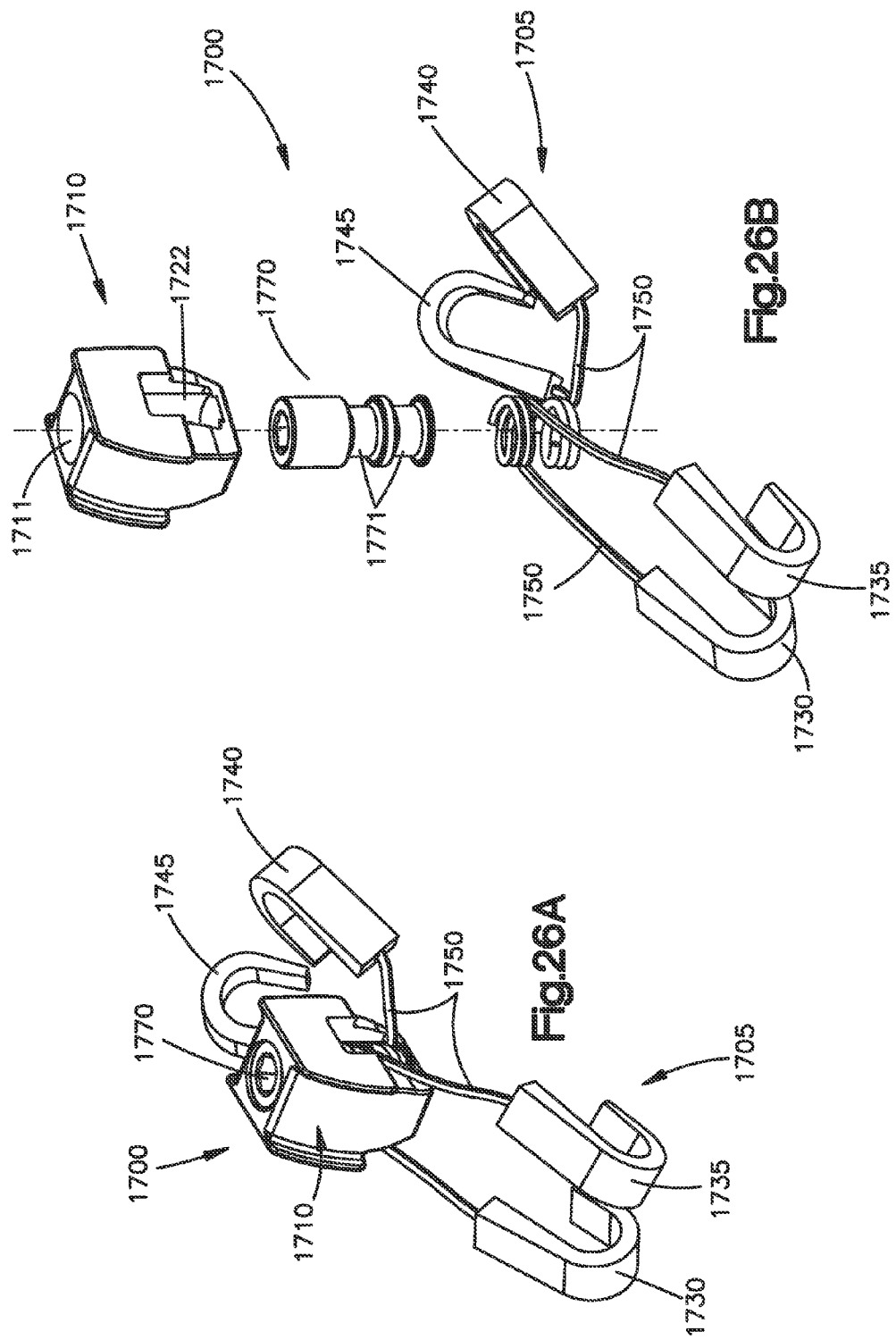

INTERSPINOUS SPACER ASSEMBLY

CROSS REFERENCE TO RELATED APPLICATIONS

This application is the National Stage of International Application No. PCT/US2009/053727, filed Aug. 13, 2009, which claims the benefit of priority to U.S. Provisional Patent Application No. 61/088,574, filed Aug. 13, 2008, the disclosures of which are hereby incorporated by reference in their entireties.

FIELD OF THE INVENTION

The present invention relates generally to orthopedics. More specifically, the present invention relates to an interspinous spacer assembly and associated methods for stabilizing the human spine.

BACKGROUND OF THE INVENTION

A human vertebra has a rearwardly projecting portion known as a spinous process. Bending or the natural aging and degeneration of the spine can cause the spinous processes of adjacent vertebrae to be moved toward each other. This constricts the space in the spinal canal and foramina and, thus, may cause pain. Such constriction, known as stenosis, can be treated by the use of an implant in the space between adjacent spinous processes.

Generally speaking there are two types of spinal stenosis: (1) hard or rigid spinal stenosis, or (2) soft or dynamic spinal stenosis. In both cases, spinal stenosis may be caused by excessive growth of tissue due to degeneration, loss of disc height, as well as disorders such as spondilolisthesis where the normal relative position and/or orientation of the adjacent vertebrae have been modified.

The most significant difference between the two types of spinal stenosis is generally that dynamic spinal stenosis may be treated with distraction of the vertebra at the affected level while hard stenosis generally requires removal of the tissue that obstructs the spinal canal or foramina at the affected level. In case of tissue removal, the patient generally must accept some loss of stability of the spine. Therefore, it is preferable to increase the stability of the spinal segment by inserting an interspinous spacer between adjacent vertebrae to increase the stiffness of the segment and/or to restrict motion of that segment. Additional stability may be desirable and may be accomplished by adding plates to rigidly fix the spacer to the spinous processes and eliminate motion at that segment (i.e. fusion).

BRIEF SUMMARY OF THE INVENTION

The present invention is directed to an interspinous spacer assembly for implantation and/or affixation between spinous processes of adjacent superior and inferior vertebrae. The interspinous spacer assembly preferably includes a spacer member sized and configured for insertion into the space between adjacent spinous processes and an engagement mechanism for operatively coupling the spacer member to the adjacent spinous processes and for preventing migration of the assembly once implanted. The interspinous spacer assembly is preferably adjustable so that the user can conform the interspinous spacer assembly to the individual anatomy of a patient's spine.

One preferred embodiment of the present invention is an interspinous spacer assembly for insertion into an interspinous space between a spinous process of a superior vertebral body and a spinous process of an inferior vertebral body. The interspinous spacer assembly may include at least one interspinous spacer member sized and configured for insertion into the interspinous space. Each spacer member may include a cranial paddle for contacting an inferior surface of the spinous process of the superior vertebral body and a caudal paddle for contacting a superior surface of the spinous process of the inferior vertebral body. The cranial paddle may be moveable with respect to the caudal paddle so that an overall height of the spacer member is adjustable. The cranial and caudal paddles each may include one of first and second lateral projections extending therefrom or first and second lateral bores formed therein. The interspinous spacer assembly may also include an engagement mechanism for operatively coupling the spacer member to the spinous processes of the superior and inferior vertebral bodies. The engagement mechanism may include a first member, a second member, a third member and a fourth member. Each of the first, second, third and fourth members may include one of a bore for receiving one of the projections extending from the cranial and caudal paddles or a projection for engaging one of the bores formed in the cranial and caudal paddles. The interacting projections and bores may enable the cranial and caudal paddles to rotate about an axis.

In alternate preferred embodiment of the present invention, the spacer member and engagement mechanism may both be formed from first, second, third and fourth interlocking plate portions such that (i) the first plate portion interlocks with the second plate portion to form an inferior portion of the spacer member for contacting the superior surface of the spinous process of the inferior vertebral body; (ii) the third plate portion interlocks with the fourth plate portion to form the superior portion of the spacer member for contacting the inferior surface of the spinous process of the superior vertebral body; (iii) the first plate portion interlocks with the third plate portion to form a first lateral plate for contacting one side of the spinous processes of the superior and inferior vertebral bodies; and (iv) the second plate portion interlocks with the fourth plate portion to form a second lateral plate for contacting a second side of the spinous processes of the superior and inferior vertebral bodies. The first, second, third and fourth plate portions may be moveably associated with respect to one another so that an overall width and an overall height of the spacer assembly are adjustable.

In another alternate preferred embodiment of the present invention, the spacer member may include a cranial paddle for contacting an inferior surface of the spinous process of the superior vertebral body, and a caudal paddle for contacting a superior surface of the spinous process of the inferior vertebral body. The spacer member may also include a spreading element for moving the cranial paddle with respect to the caudal paddle to adjust an overall height of the spacer member. The engagement mechanism may include first and second members operatively coupled to one another.

In another alternate preferred embodiment of the present invention, the spacer member may include a cranial spacer portion for contacting an inferior surface of the superior spinous process and a caudal spacer portion for contacting a superior surface of the inferior spinous process. The cranial spacer portion may be moveably coupled to the caudal spacer portion by a ratchet mechanism so that an overall height of the spacer member is adjustable. The ratchet mechanism may include a plurality of teeth formed on an anterior end and a posterior end of the caudal spacer portion for engaging at least one tooth formed on an anterior end and a posterior end of the cranial spacer portion.

In another alternate preferred embodiment of the present invention, the spacer member may include a cranial surface for contacting an inferior surface of the spinous process of the superior vertebral body, and a caudal surface for contacting a superior surface of the spinous process of the inferior vertebral body. The space member may also include a bore extending therethrough, wherein at least a portion of the engagement mechanism passes through the bore formed in the spacer member. The engagement mechanism may also include a plurality of rotatable wings extending from the spacer member for laterally engaging the spinous processes. The plurality of rotatable wings may be rotatable from a first folded configuration to a second deployed configuration.

In another alternate preferred embodiment of the present invention, the spacer member and engagement mechanism may be formed from first and second interlocking members such that the first member interlocks with the second member. The first and second members may be moveably associated with respect to one another and the spacer may have an adjustable width and height.

In another alternate preferred embodiment of the present invention, the spacer member and engagement mechanism may be formed from a first member, a second member and an intermediate spacer part. The first member may include a cranial spacer part for contacting an inferior surface of the spinous process of the superior vertebral body and a first wing for contacting a first lateral side of the superior vertebral body. The second member may include a caudal spacer part for contacting a superior surface of the spinous process of the inferior vertebral body and a second wing for contacting a first lateral side of the inferior vertebral body. The intermediate spacer part may be slidably disposed between the cranial spacer part and the caudal spacer part of the first and second members. The intermediate spacer part may also be operatively associated with a third wing and a fourth wing of the first and second members for contacting a second lateral side of the superior and inferior vertebral body, respectively.

In another alternate preferred embodiment of the present invention, the spacer member may include a cranial surface for contacting an inferior surface of the spinous process of the superior vertebral body, a caudal surface for contacting a superior surface of the spinous process of the inferior vertebral body. The spacer member may also include a ventral end and a dorsal end. The interspinous spacer member may include one of a bore and a clip and the engagement mechanism may include the other one of the bore and the clip. The bore may be operatively associated with the clip so that the interspinous spacer member is rotatable with respect to the engagement mechanism.

BRIEF DESCRIPTION OF THE SEVERAL VIEWS OF THE DRAWINGS

The foregoing summary, as well as the following detailed description of preferred embodiments of the application, will be better understood when read in conjunction with the appended drawings. For the purposes of illustrating the preferred interspinous spacer assemblies of the present application, drawings of the preferred embodiments are shown. It should be understood, however, that the application is not limited to the precise arrangements, structures, features, embodiments, aspects, and instrumentalities shown, and the arrangements, structures, features, embodiments, aspects, and instrumentalities shown may be used singularly or in combination with other arrangements, structures, features, embodiments, aspects and instrumentalities. In the drawings:

FIG. 3A illustrates a side perspective view of an exemplary embodiment of a single headed bone screw that may be used in combination with the interspinous spacer assembly shown in FIG. 1;

FIG. 3B illustrates a side perspective view of an exemplary embodiment of a double headed bone screw that may be used in combination with interspinous spacer assembly shown in FIG. 1;

FIG. 4A is a partially exploded side perspective view of the interspinous spacer assembly show in FIG. 1;

FIG. 4B is a cross-sectional view of the interspinous spacer assembly taken along line 4B-4B from FIG. 4A;

FIG. 6A is a posterior elevational view of the interspinous spacer assembly shown in FIG. 5, the interspinous spacer assembly being in a first, collapsed configuration;

FIG. 6B is a posterior elevational view of the interspinous spacer assembly shown in FIG. 5, the interspinous spacer assembly being in a second, expanded configuration;

FIG. 7 illustrates a side perspective view of a third preferred embodiment of an interspinous spacer assembly in accordance with the present invention;

FIG. 8 illustrates a side perspective view of a fourth preferred embodiment of an interspinous spacer assembly in accordance with the present invention;

FIG. 9 illustrates a side perspective view of a fifth preferred embodiment of an interspinous spacer assembly in accordance with the present invention;

FIG. 10 illustrates a side perspective view of an exemplary insertion instrument for use in holding, distracting and locking the interspinous spacer assembly shown in FIG. 9;

FIG. 12A illustrates a side perspective view of a seventh preferred embodiment of an interspinous spacer assembly in accordance with the present invention;

FIG. 12B illustrates a side elevational view of the interspinous spacer assembly shown in FIG. 12A;

FIG. 13A illustrates a side elevational view of an eighth preferred embodiment of an interspinous spacer assembly according to the present invention, the interspinous spacer assembly being in a non-expanded, collapsed configuration;

FIG. 13B illustrates a side elevational view of the interspinous spacer assembly shown in FIG. 13A, the interspinous spacer assembly being in an expanded, deployed configuration;

FIG. 13C illustrates a side elevational view of the interspinous spacer assembly shown in FIG. 13A, the interspinous spacer assembly being in an incremental configuration between the non-expanded, collapsed configuration shown in FIG. 13A and the expanded, deployed configuration shown in FIG. 13B;

FIG. 13D illustrates a side perspective view of the interspinous spacer assembly shown in FIG. 13A coupled to adjacent spinous processes;

FIG. 19 illustrates a side perspective view of an eleventh preferred embodiment of an interspinous spacer assembly according to the present invention;

FIG. 20 illustrates a partial, side perspective view of a twelfth preferred embodiment of an interspinous spacer assembly according to the present invention, the interspinous spacer assembly including the interspinous spacer member shown in FIG. 19 with an adjustable engagement mechanism for adjustably coupling the spacer member to adjacent spinous processes, the adjustable engagement mechanism being configured as a multilevel construct;

FIG. 21 illustrates a partial, side perspective view of a thirteenth preferred embodiment of an interspinous spacer assembly according to the present invention;

FIG. 22 illustrates a side perspective view of the interspinous spacer assembly shown in FIG. 21 coupled to adjacent spinous processes;

FIG. 23A illustrates a side perspective view of a fourteenth preferred embodiment of an interspinous spacer assembly according to the present invention;

FIG. 23B illustrates an exploded, side perspective view of the interspinous spacer assembly shown in FIG. 23A;

FIG. 24A illustrates an anterior perspective view of a fifteenth preferred embodiment of an interspinous spacer assembly according to the present invention;

FIG. 24B illustrates a posterior perspective view of the interspinous spacer assembly shown in FIG. 24A;

FIG. 25A illustrates a side perspective view of a sixteenth preferred embodiment of an interspinous spacer assembly according to the present invention;

FIG. 25B illustrates an exploded, side perspective view of the interspinous spacer assembly shown in FIG. 25A;

FIG. 25C illustrates a top elevational view of the interspinous spacer assembly shown in FIG. 25A;

FIG. 25D illustrates a side perspective view of the interspinous spacer assembly of FIG. 25A coupled to adjacent spinous processes;

FIG. 26A illustrates a side perspective view of a seventeenth preferred embodiment of an interspinous spacer assembly according to the present invention;

FIG. 26B illustrates an exploded, side perspective view of the interspinous spacer assembly shown in FIG. 26A.

DETAILED DESCRIPTION OF THE INVENTION

Figure 2:
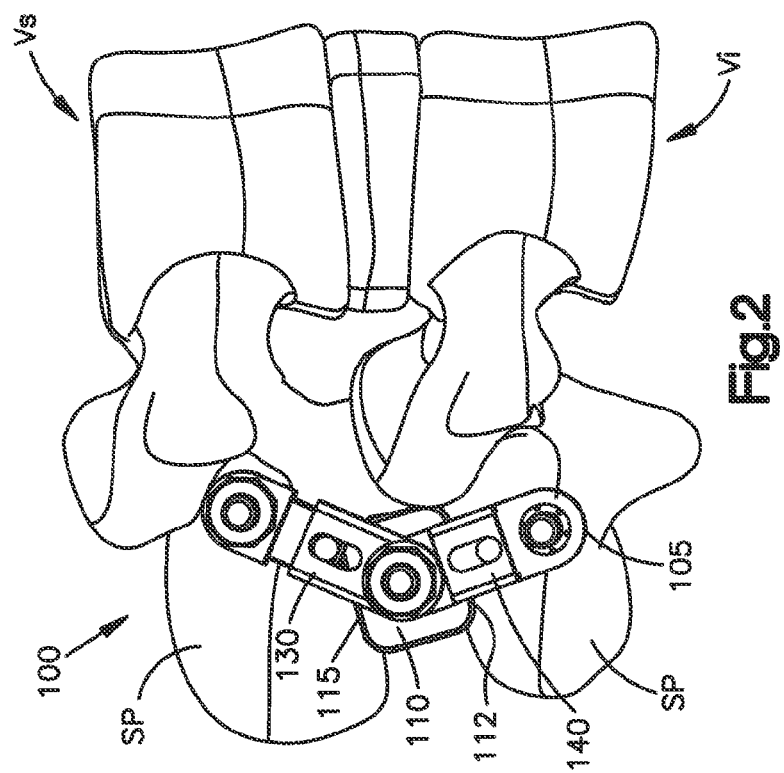
FIG. 2 illustrates a side elevational view of the interspinous spacer assembly shown in FIG. 1.
Figure 1:
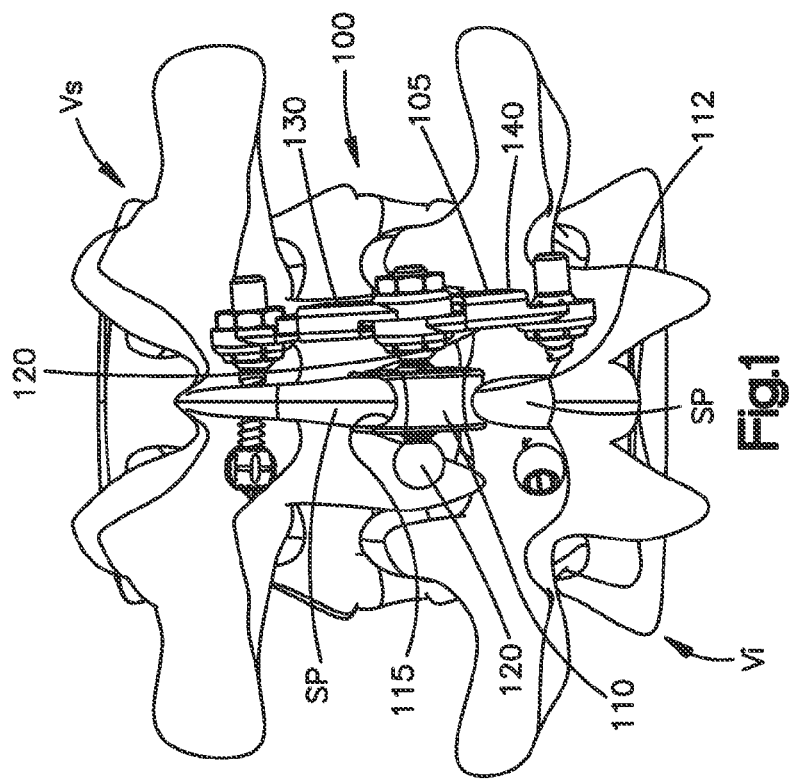
FIG. 1 illustrates a posterior elevational view of a first preferred embodiment of an interspinous spacer assembly according to the present invention mounted to superior and inferior vertebrae.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the interspinous spacer and designated parts thereof. The words "anterior", "posterior", "superior", "inferior" and related words and/or phrases designate preferred positions and orientations in the human body to which reference is made and are not meant to be limiting. The words and phrases "collapse", "telescopic", "disposed within", "slidably disposed within", "interlock" and related words and/or phrases designate the relationship between two parts or devices to which reference is made and are not meant to limiting. The terminology includes the above-listed words, derivatives thereof and words of similar import.

Certain exemplary embodiments of the invention will now be described with reference to the drawings. In general, such embodiments relate to an interspinous spacer assembly for implantation and/or affixation between spinous processes SP of adjacent vertebrae, including a superior vertebra Vs and an inferior vertebra Vi to treat spinal stenosis or any condition wherein spacing between the spinous processes SP of the adjacent vertebrae Vs, Vi is desired.

As will be described in greater detail below, the interspinous spacer assembly preferably includes an interspinous spacer member sized and configured for insertion into the space between adjacent spinous processes SP and an engagement mechanism for operatively coupling the spacer member to one or more of the adjacent spinous processes SP. The interspinous spacer assembly is preferably adjustable so that the user can configure the interspinous spacer assembly to fit the anatomy of the patient's spine. The interspinous spacer assembly may be fully or partially adjustable. For example, the height, width and/or angle of the spacer assembly may be adjustable. Alternatively, only the height, only the width or only the angle of the spacer member may be adjustable, or the spacer member may be non-adjustable. Moreover, the height, width and/or the angle of the spacer member may be adjustable to only a certain extent or limit. Additionally, the engagement mechanism is preferably adjustable so that the user can adjust the engagement mechanism such as, for example, the orientation, height, width, etc., as necessary to engage the patient's spinous processes SP. Alternatively, in some embodiments, the adjustability of the engagement mechanism may be limited or non-adjustable. Likewise, the method of implanting the interspinous spacer preferably allows a surgeon to adjust the interspinous spacer and/or the orientation of the interspinous spacer in the patient.

The interspinous spacer assembly of the present invention may be implanted using a number of different approaches. For example, the interspinous spacer assembly may be inserted laterally into the interspinous space or it may be implanted via a range of different posterior approaches, preferably without disruption, damage or removal of the spinal ligaments (e.g. ligaments remain intact), although, the ligaments may be disrupted, damaged, cut and/or removed to facilitate implantation of the interspinous spacer assembly or portions thereof. Although the interspinous spacer assembly of the present invention generally allows for a less invasive implantation procedure, different embodiments of the present invention may require varying degrees of invasiveness during implantation. The lateral approach of implanting the interspinous spacer assembly may be less invasive than posterior approaches. One less invasive implantation procedure, may allow an interspinous spacer member of the interspinous spacer assembly of the present invention to be implanted between adjacent spinous processes SP and be coupled to adjacent spinous processes SP via an engagement mechanism fixed to adjacent spinous processes SP at the interface of the supra spinous ligament and the spinous processes SP, thus preserving the muscles attached to the spinous processes SP.

The interspinous spacer assembly may be used to treat spinal stenosis in combination with decompression. Alternatively, the interspinous spacer assembly may be used to treat spinal stenosis without any additional treatment. Especially in the situation where decompression is used, it is desirable to restore at least part of the stability of the spine with an interspinous spacer assembly.

In use, the interspinous spacer assembly of the present invention, may allow for application of distractive force as well as a compressive force to the same spinal level (e.g. distractive force in case of extension of the spine and compressive force in case of flexion of the spine).

In certain embodiments of the present invention, the interspinous spacer assembly includes an interspinous spacer member and an engagement mechanism for engaging one or more of the spinous processes SP. The engagement mechanism may include wings, plates, hooks, etc. that prevent migration of the interspinous spacer assembly. In certain embodiments the engagement mechanism may be adjustable in length, bendable, polyaxial with respect to the spacer member, etc. to enable adaptability to the individual anatomy of a particular patient's spine and prevent migration of the interspinous spacer assembly once implanted into the patient. In use, the engagement member may engage the patient's spinous processes SP in a variety of different ways including, for example, via one or more screws, bolts, rivets, spikes, or other protrusions and/or via compression. The engagement mechanism may be operatively coupled to the interspinous spacer member or members in a variety of different ways. One having ordinary skill in the art will recognize that the various engagement mechanisms described for the preferred embodiments of the interspinous spacer assemblies may be adapted and interchanged between the interspinous spacer assemblies of preferred embodiments, without significantly impacting the structure and operation of the implants.

In certain embodiments of the present invention, the interspinous spacer member of the interspinous spacer assembly may be made from several parts, for example, two interspinous spacer paddles or spacer plates may function as the spacer member, such that each paddle or plate contacts one of the adjacent spinous processes SP. The spacer paddles or plates are preferably adjustable with respect to one another so that the height of the spacer member can be adjusted or the distance between the paddles can be modified. Additionally, in other embodiments, the interspinous spacer may be formed by parts that serve multiple functions.

The interspinous spacer assembly and components thereof may be made from any biocompatible material including but not limited to metals such as, e.g., titanium, titanium alloys, stainless steel, etc., polymers such as, e.g., PEEK, PCU, etc., and combinations thereof. In the situation where the interspinous spacer assembly may be manufactured from PEEK, the combination of an elastic rubber like polymer may be used to allow for any large deformations and high loads that may be encountered by the interspinous spacer assembly.

The interspinous spacer assembly may also promote spinal fusion for example, by constructing the spacer member from a mesh or porous type material or structure. Alternatively and/or in addition, perforations or cavities may be formed in the spacer member. The method of implanting the interspinous spacer assembly may also promote spinal fusion. For example, a surgeon implanting the interspinous spacer assembly between adjacent spinous processes SP may also implant bone chips or other biocompatible implant material that fuses with the adjacent spinal processes through cavities or pores formed in the interspinous spacer assembly.

Referring to FIGS. 1-4B, a first preferred embodiment of the interspinous spacer assembly 100 includes an interspinous spacer member 110 sized and configured for insertion into an interspinous space between adjacent spinous processes SP and an engagement mechanism 105 for operatively coupling the spacer member 110 to the adjacent spinous process SP.

The spacer member 110 may be designed as a non-adjustable, rigid body, although it is envisioned that an adjustable spacer member such as those described herein with respect to certain of the other preferred embodiments may be used. The spacer member 110 preferably includes a caudal spacer portion 112 for contacting a superior surface of the inferior spinous process SP and a cranial spacer portion 115 for contacting an inferior surface of the superior spinous process SP. The bone contacting surfaces of the cranial and caudal spacer portions 115, 112 preferably include seats (e.g., concave or U-shaped recesses, See FIG. 1) for receiving the adjacent spinous processes SP. In use, the spacer member 110 may be configured such that it is implanted at the posterior ends of the adjacent spinal processes SP or further toward the anterior of the adjacent spinal processes SP.

The spacer member 110 may also include a projection 120 extending from one or both of the lateral sides thereof for engaging the engagement mechanism 105. In use, the engagement mechanism 105 may be implanted on either one (unilateral construct) or both sides (bilateral construct) of the spacer member 110 and adjacent to the spinous processes SP. More preferably, the spacer member 110 includes one or more curvate or spherical projections 120 for engaging a pop-on coupling mechanism 170 operatively associated with the engagement mechanism 105, as will be described in greater detail below, so that the engagement mechanism 105 may polyaxial rotate with respect to the spacer member 110. This configuration enables the user to adjust the position of the engagement mechanism 105 with respect to the spacer member 110. It should be noted that other types of coupling mechanisms may be used, for examples, interconnecting threads, screws, rivets, bolts, etc.

The engagement mechanism 105 may be in the form of one or more plates 130, 140 for coupling the spacer member 110 to the adjacent spinous processes SP. As shown, the engagement mechanism 105 is preferably in the form of first and second plate assemblies 130, 140 for coupling the spacer member 110 to the adjacent upper and lower spinous processes SP.

The plate assemblies 130, 140 preferably have adjustable lengths and can be adjusted to accommodate various fixation angles with respect to the spacer member 110. The adjustability of the lengths of the plates 130, 140 is preferably achieved through a telescopic construction of the plates 130, 140. For example, each of the plate assemblies 130, 140 of the first preferred embodiment includes a female portion 131, 141 and a male portion 132, 142 whereby the male portion 132, 142 is slidably received within the female portion 131, 141 so that the overall length of the assemblies 130, 140 can be adjusted.

The plates assemblies 130, 140 are preferably connected to the adjacent spinous processes SP and/or laminae via one or more bone fixation elements, more preferably bone screws 160. The bone screws 160 preferably include an enlarged, curvate or semi-spherical head portion 162 and an externally threaded shaft portion 163 for engaging the patient's spinal processes. The head portion 162 preferably includes a mechanism for engaging a screwdriver (not shown). For example, the head portion 162 preferably includes a plurality of recesses for engaging a plurality of projections formed on a tip of a screwdriver, although other configurations are envisioned, including but not limited to, an internal recess, an external hexagon, a star drive pattern, a Phillips head pattern, a slot for a screw driver, a threading for a correspondingly threaded post, etc.

The specific features of the shaft 163 including, for example, thread pitch, self drilling configurations, self tapping configurations, shaft diameter, shaft shape, etc. are interchangeable, and it would be apparent to one having ordinary skill in the art that the bone screws 160 are not limited to any particular type of shaft 163 or thread configuration. The bone screw 160 may also include a reduced diameter neck portion between the head portion 162 and the shaft portion 163, which accommodates the polyaxial connection of the bone screws 160 to the plate assemblies 130, 140. The bone screws 160 may further be cannulated and fenestrated (not shown) such that openings extend outwardly from a central hollow channel in a cannulated screw to urge fluid out of the screws 160 during injection or draw fluid into the central hollow channel from sides of the screw 160 during extraction of material adjacent the screws 160.

Referring to FIG. 3A, the screws 160 may include a single head portion 162 as is generally known in the art. Alternatively, referring to FIG. 3B, the screws 160 may include dual head portions. That is, a second head portion 164 may be attached to the threaded shaft portion 163 of a first bone screw 160 after the first screw 160 has been inserted into and through the spinous process SP. In this manner, a bilateral construct, wherein plates 130, 140 are placed on both lateral sides of the spinous processes SP, may be coupled to the same bone screw 160. It should be noted, that in bilateral constructs, it is not necessary to use double-headed screws. For example, single head screws may be inserted into the spinous processes SP on both sides of the spinous processes SP.

The plate assemblies 130, 140 of the first preferred embodiment can be mounted to the curvate head portion 162 of the bone screws 160 and to the curvate projection 120 extending from the spacer member 110 by any coupling means or mechanism now or hereafter known in the art. Preferably, however, the plate assemblies 130, 140 are mounted to the screws 160 and to the spacer member 110 by a pop-on mechanism 170 so that the plate assemblies 130, 140 can be coupled to the bone screws 160 and the spacer member 110 after the bone screws 160 and the spacer member 110 have been implanted, thus allowing visibility during screw insertion and simplifying the surgical technique.

Referring to FIG. 4B, the pop-on mechanism 170 of the first preferred embodiment includes a flexible collet 172 having a semi-spherical recess 173 for receiving the curvate or semi-spherical head portion 162 of the bone screws 160 and the curvate projection 120 extending from the spacer member 110. The collet 172 includes a threaded second end 174 extending therefrom so that the threaded end 174 of the collet 172 may extend through a hole or slot formed in the plate assemblies 130, 140 before engaging a nut member 176. In use, after the spacer member 110 has been inserted into the interspinous space, the bone screws 160 have been inserted into the adjacent spinous processes SP and the plate assemblies 130, 140 have been properly orientated and coupled to the bone screws 160 and the spacer member 110, the user may rotate the nut member 176, which in turn causes the collet 172 to move with respect to the hole or slot formed in the plate assemblies 130, 140, thereby causing the collet 172 to compress against the curvate head portion 162 of the bone screw 160 and projection 120 to secure the relative position of the plate assemblies 130, 140 with respect to the spacer member 110 and the bone screws 160.

In the case of a bilateral construct, the plates 130, 140 are installed on both sides of the interspinous spacer 110 and a second pop-on coupling mechanism 170 is provided to engage the spherical projection 120 extending from the spacer member 110 for coupling the spacer member 110 to the additional set of plates 130, 140 as well as coupling the plates 130, 140 to each other.

Alternatively, it is envisioned that one or more spinal rods (not shown) can be used in place of the preferred plates 130, 140. In addition, the bone screws 160 may be secured in the spinous process SP or in the pedicles of the vertebrae Vs, Vi. Alternatively, it is envisioned that the system may be used without a spacer member 110 implanted between the adjacent vertebrae Vs, Vi.

Both single and multilevel constructs for implantation of multiple interspinous spacer assemblies 100 of the first preferred embodiment at multiple levels are possible and such constructs would be apparent to one having ordinary skill in the art based upon a review of the present application.

Figure 5:
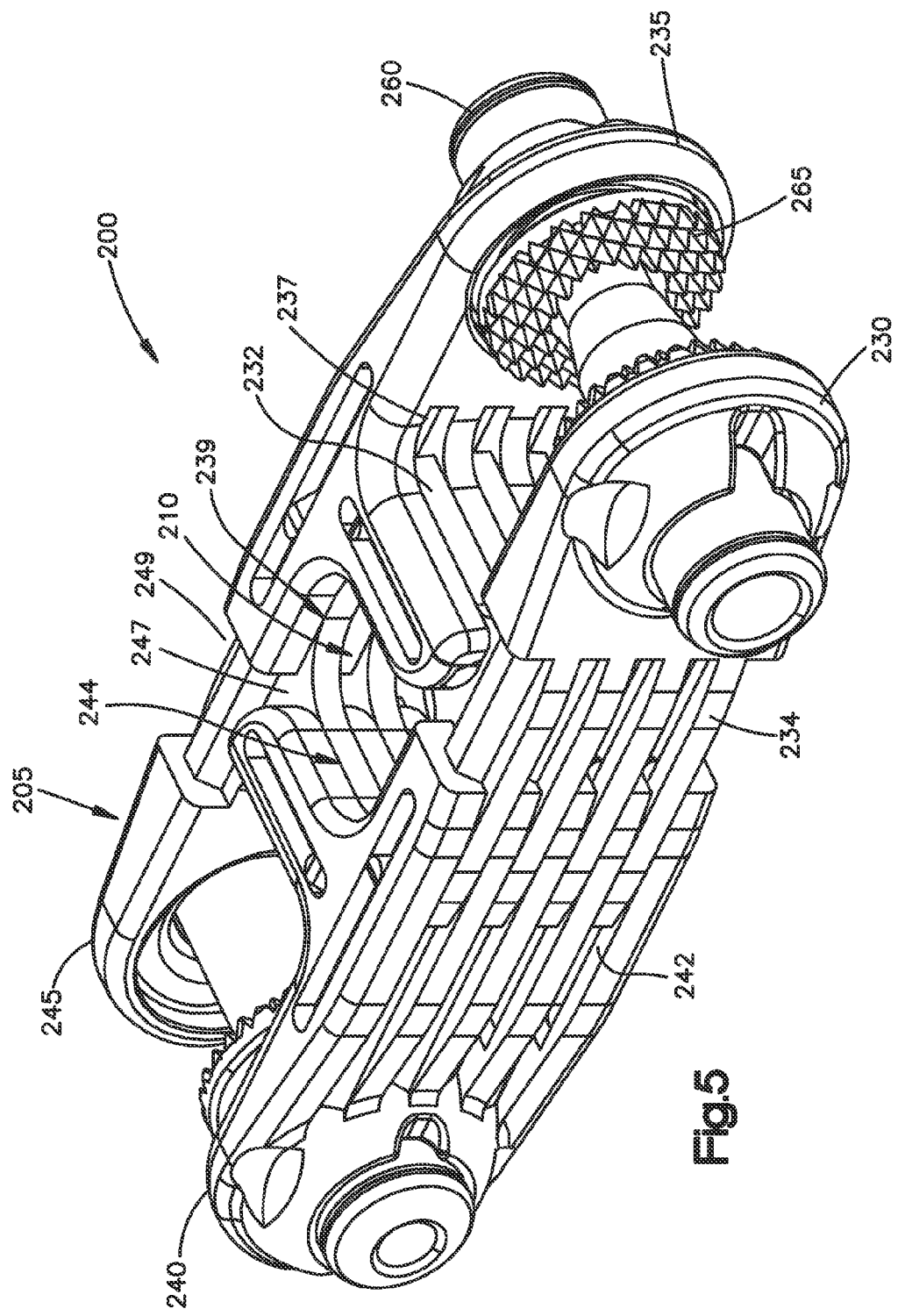
FIG. 5 illustrates a side perspective view of a second preferred embodiment of an interspinous spacer assembly in accordance with the present invention.

Referring to FIGS. 5-6B, a second preferred embodiment of the interspinous spacer assembly 200 includes an integrated, adjustable spacer member 210 and an engagement mechanism 205 so that the interspinous spacer assembly 200 can be adapted to various sized spinous processes SP and spaces therebetween. The interspinous spacer assembly 200 (e.g., spacer member 210 and engagement mechanism 205) is preferably adjustable in both length and width to conform to the patient's anatomy. The interspinous spacer assembly 200 of the second preferred embodiment includes four plates portions 230, 235, 240, 245 that form the adjustable spacer member 210 and engagement mechanism 205.

The four plate portions 230, 235, 240, 245 preferably interlock with one another to form both the spacer member 210 and lateral plates (i.e., engagement member 205) used for engaging the spinous processes SP. For example, a first plate portion 230 interlocks with a second plate portion 235 to form an inferior portion of the interspinous spacer assembly 200 for contacting the superior portion of the inferior spinous process SP while a third plate portion 240 interlocks with a fourth plate portion 245 to form the superior portion of the interspinous spacer assembly 200 for contacting the inferior portion of the superior spinous process. The first plate portion 230 also interlocks with the third plate portion 240 to form a first lateral plate for engaging the lateral portions of one side of the adjacent spinous processes SP while second plate portion 235 interlocks with fourth plate portion 245 to form a second lateral plate for engaging the lateral portion of a second side of the adjacent spinous processes SP.

The plate portions 230, 235, 240, 245 may interlock with one another by any means now or hereafter known for such purpose. The plate portions 230, 235, 240, 245 of the second preferred embodiment interlock via a series of interlocking rails and grooves. For example, as best shown in FIG. 5, the first plate portion 230 includes a plurality of rails 232 disposed within and/or between grooves 237 formed in the second plate portion 235 in order to form the inferior portion of the adjustable spacer member 210. In use, the rails 232 are slidably disposable with respect to the grooves 237 so that the position of the first plate portion 230 may be laterally adjusted with respect to second plate portion 235. Similarly, the first plate portion 230 may include a plurality of rails 234 disposed within and/or between grooves 242 formed in the third plate portion 240 in order to form one of the lateral side plates. In use, the rails 234 are slidably disposable with respect to the grooves 242 so that the position of the first plate portion 230 may be vertically adjusted with respect to the third plate portion 240. Likewise, the fourth plate portion 245 may include a plurality of rails 247 disposed within and/or between grooves 244 formed in the third plate portion 240 in order to form the superior portion of the adjustable spacer member 210. In use, the rails 247 are slidably disposable with respect to the grooves 244 so that the position of the fourth plate portion 245 may be laterally adjusted with respect to the third plate portion 240. Similarly, the fourth plate portion 245 may include a plurality of rails 249 disposed within and/or between grooves 239 formed in the second plate portion 235 in order to form the second lateral plate. In use, the rails 249 are slidably disposable with respect to the grooves 239 so that the position of the second plate portion 235 may be vertically adjusted with respect to the fourth plate portion 245.

In this manner, the user can fully adjust the height and width of the spacer member 210 of the second preferred embodiment and the height and width of the engagement mechanism (i.e., lateral plates 230, 235, 240, 245) to conform to the patient's anatomy. The interspinous spacer assembly 200 of the second preferred embodiment is adjustable from a first, collapsed configuration (as shown in FIG. 6A) so that the height and width of the spacer member 210 and engagement mechanism (i.e., lateral plates 230, 235, 240, 245) is minimized to facilitate insertion, to a second, expanded configuration (as shown in FIG. 6B) so that the height and width of the spacer member 210 and the height and width of the engagement mechanism (i.e., lateral plates 230, 235, 240, 245) are increased. The arrangement of the second preferred embodiment of the interspinous spacer assembly 200 further enables the user to select amongst any number of intermediate configurations. Alternatively, in a first configuration, the interspinous spacer assembly 200 may have a minimized height and a maximized width to facilitate insertion of the interspinous spacer assembly 200 into the interspinous space, the user may then distract the interspinous spacer assembly 200 to the desired height and then reduce its width so that the assembly holds the spinous processes SP between the lateral plates 230, 235, 240, 245.

The second preferred embodiment of the interspinous spacer assembly 200 may be manufactured from a polymer such as, for example, PEEK or any other weldable polymer so that the position of the engagement mechanism (i.e., lateral plates 230, 235, 240, 245) can be secured by, for example, ultrasonic welding. Alternatively, the interspinous spacer assembly 200 can be manufactured from any other biocompatible material wherein the position of the engagement mechanism (i.e., lateral plates 230, 235, 240, 245) may be secured by any other means including, for example, mechanical means such as screws, ratchet, etc.

The interspinous spacer assembly 200 of the second preferred embodiment may be coupled to the spinous processes SP by any means now or hereafter known in the art. Preferably, the engagement mechanism (i.e., lateral plates 230, 235, 240, 245) is secured to the adjacent spinous processes SP by a bolt mechanism 260. In use, the bolt mechanism 260 is inserted through the spinous process SP from one or both sides. For example, as best shown in FIGS. 6A and 6B, the bolt mechanism 260 may include a female portion 261 and a male portion 262 extending from the spacer assembly 200 that is laterally insertable into one of the spinous processes SP. The preferred male portion 262 is mateable with the female portion 261 so that the bolt mechanism 260 adapts to various spinous process thicknesses. The bolt mechanism 260 may also include washers 265, more preferably spiked washers, for engaging the adjacent spinous processes SP. The bolt mechanism 260 may be replaced by any other mechanism for coupling the engagement mechanism 205 to the adjacent spinous processes SP described herein or known for such purpose including, for example, threaded bolts and nuts, bone screws, friction fit, press fit, etc.

Referring to FIG. 7, a third preferred embodiment of the interspinous spacer assembly is similar to the interspinous spacer assembly 200 of the second preferred except as noted below. The interspinous spacer assembly 300 of the third preferred embodiment is preferably manufactured from titanium or similar biocompatible material. In the third preferred embodiment, an engagement mechanism 305 (i.e., plate portions 330, 335, 340, 345) preferably includes single interlocking male and female portions (as opposed to a plurality of interlocking rail and grooves as described above in connection with interspinous spacer assembly 200). For example, a second plate portion 335 include a single female portion or recess 337 for engaging a single male portion 347 extending from a fourth plate portion 345 so that the fourth plate portion 345 is telescopingly received within the second plate portion 335. Similarly, a third plate portion 340 includes a single female portion or recess 342 for engaging a single male portion 332 extending from a first plate portion 330 so that the first plate portion 330 is telescopingly received within the third plate portion 340. Likewise, the second plate portion 335 includes a single female portion or recess 339 for engaging a single male portion 334 extending from the first plate portion 330 so that the first plate portion 330 is telescopingly received within the second plate portion 335 and the third plate portion 340 includes a single female portion or recess 344 for engaging a single male portion (not shown) extending from the fourth plate portion 345 so that the fourth plate portion 345 is telescopingly received within the third plate portion 340. Although it is envisioned that each plate portion 330, 335, 340, 345 may include more than one interlocking male and female portion.

In the construction of the third preferred embodiment of the interspinous process spacer assembly 300, the user can fully adjust the height and width of the spacer member 305 and the height and width of the engagement mechanism (i.e., lateral plates 330, 335, 340, 345) to conform to the patient's anatomy. The interspinous spacer assembly 300 of the third preferred embodiment is adjustable from a first, collapsed configuration so that the height and width of the spacer member 310 and engagement mechanism (i.e., lateral plates 330, 335, 340, 345) is minimized, to a second, expanded configuration so that the height and width of the spacer member 310 and the height and width of the engagement mechanism (i.e., lateral plates 330, 335, 340, 345) is maximized. The arrangement of the third preferred embodiment of the spinous spacer assembly 300 further enables the user to select amongst any number of intermediate configurations between the expanded and collapsed configurations. Alternatively, in a first configuration, the interspinous spacer assembly 300 of the third preferred embodiment may have a minimized height and a maximized width to facilitate insertion of the interspinous spacer assembly 300 into the interspinous space, the user may then distract the interspinous spacer assembly 300 to the desired height and reduce its width so that the assembly holds the spinous processes SP between the lateral plates 330, 335, 340, 345.

After the interspinous spacer assembly 300 of the third preferred embodiment is adjusted to adapt to the patient's anatomy, the position of the engagement mechanism (i.e., lateral plates 330, 335, 340, 345) may be secured to one another by any mechanism known in the art including, but not limited to, friction fit, press-fit, a bolt mechanism, a ratchet mechanism, etc. Preferably, the position of the engagement mechanism (i.e., lateral plates 330, 335, 340, 345) is secured by set screws 380.

In addition, the interspinous spacer assembly 300 of the third preferred embodiment may be coupled to the adjacent spinous processes SP by any means now or hereafter known in the art. For example, as shown, the spacer assembly 300 may be secured to the adjacent spinous processes SP with rotatable spikes 361, which, in use, may be engaged via a tool and rotated to engage and/or pierce the spinous processes SP. The rotatable spike 361 may include a series of smaller spikes for engaging the spinous process SP surrounded by a larger central spike for piercing the spinous process SP. Alternatively, the spikes 361 may be ratchetably coupled to the engagement mechanism (i.e., lateral plates 330, 335, 340, 345) so that the spikes 361 can be linearly (i.e., non-rotatably) moved into engagement with the adjacent spinous processes SP. In another arrangement, the rotatable spikes 361 for fixing the engagement mechanism (i.e., lateral plates 330, 335, 340, 345) to the spinous processes SP may be replaced with a linear ratchet mechanism, shown in FIG. 15 and described below. In other arrangements, the rotatable spikes 361 for fixing the engagement mechanism (i.e., lateral plates 330, 335, 340, 345) to the spinous processes SP may be replaced by any other mechanism described herein or known for such purpose including, for example, a bolt mechanism, rivets, threaded bolts and nuts, bone screws, etc.

Referring to FIG. 8, a fourth preferred embodiment of the interspinous spacer assembly 400 is similar to the interspinous spacer assembly 300 of the third preferred embodiment except as noted below. In the fourth preferred embodiment, the position of the engagement mechanism (i.e., lateral plates 430 (not shown), 435, 440 (not shown), 445) may be secured by a ratchet-mechanism 450 that is integrally formed with the engagement mechanism 405.

More specifically, second and fourth plate portions 435, 445 preferably include a single interlocking male and female portion. For example, the second plate portion 435 includes a single female portion or recess 437 for engaging a single male portion 447 extending from the fourth plate portion 445 so that the fourth plate portion 445 may be telescopingly received within the second plate portion 435. However, it is envisioned that the second and fourth plate portions 435, 445 of the fourth preferred embodiment may include more than one interlocking male and female portion.

In use, the user can fully adjust the height and width of the spacer member 410 and the height and width of the engagement mechanism (i.e., lateral plates 435, 445) to conform to the patient's anatomy. The position of the lateral plates 435, 445 are preferably fixed with respect to one another via a ratchet mechanism 450. As shown in FIG. 8, for example, the fourth plate portion 445 may include a projection 448 extending from the male portion 447, the projection 448 having a plurality of teeth for engaging a recess 451 formed in the female portion 437 of the second plate portion 435, the recess 451 having a plurality of grooves for interlocking with the plurality of teeth formed on the projection 448.

Referring to FIG. 9, a fifth preferred embodiment of an interspinous spacer assembly 500 includes an interspinous spacer member 510 having a cranial spacer paddle 512 for contacting an inferior surface of the superior spinous process SP and a caudal spacer paddle 515 for contacting a superior surface of the inferior spinous process SP. The cranial spacer paddle 512 is preferably movable with respect to the caudal spacer paddle 515 so that the height of the spacer member 510 can be adjusted to fit a patient's anatomy.

The cranial spacer paddle 512 is preferably integrally formed with the engagement mechanism 505, which is in the form of cranial wings 540, 545 for coupling the cranial spacer paddle 512 to the superior adjacent spinous process SP. Likewise, the caudal spacer paddle 515 is preferably integrally formed with caudal wings 530 for coupling the caudal spacer paddle 515 to the inferior adjacent spinous process SP. However, as will be readily appreciated by one of ordinary skill in the art, the cranial and caudal spacer paddles 512, 515 may be separately formed and operatively coupled to the cranial and caudal wings 540, 545, 530, 535 by any means now or hereafter known for such purpose.

The caudal spacer paddle 515 and the caudal wings 530 preferably include an integrated rack assembly 531, which is telescopingly received in a recess 541 formed in the cranial spacer paddle 512 and the cranial wings 540, 545 thereby adjustably couple the cranial spacer paddle 512 to the caudal spacer paddle 515 so that the height of the interspinous spacer assembly 500 of the fifth preferred embodiment can be adjusted. Once properly positioned, a set screw (not shown) disposed in a screw recess 581 may be used to secure the position of the interspinous spacer assembly 500.

The caudal spacer paddle 515 and the caudal wings 530 and the cranial spacer paddle 512 and the cranial wings 540, 545 preferably include recesses 585, 586, respectively, for reasons that will be described below.

In use, the cranial and caudal wings 530, 540, 545 may be coupled to the adjacent spinous processes SP by a bolt mechanism 560, as previously described. Alternatively, the cranial and caudal wings 530, 540, 545 may be coupled to the adjacent spinous processes SP by any other mechanism described herein or known for such purposes.

Referring to FIG. 10, an exemplary insertion instrument 590 is illustrated for inserting the interspinous spacer assembly 500 of the fifth preferred embodiment. The insertion instrument 590 preferably includes a handle 591, a multilayer screw shaft 592 having a tool tip 593, a holding knob 594, a distracting knob 595 and a locking knob 596. The tool tip 593 of the multilayer screw shaft 592 preferably includes a set screw engaging device for engaging the set screw disposed in screw recess 581 for securing the cranial and caudal paddles 512, 515.

In use, the tool tip 593 preferably includes a plurality of hooks 593a for engaging the recesses 585, 586 formed in the interspinous spacer assembly 500 of the fifth preferred embodiment. The tool tip 593 is operatively associated with the holding knob 594 so that rotation of the holding knob 594 firmly couples the interspinous spacer assembly 500 to the insertion tool 590. The assembly distracting device of the multilayer screw shaft 592 operatively engages the rack assembly 531 and the set screw engaging device operatively engages the set screw disposed in the screw recess 581 so that rotation of the assembly distracting knob 595 distracts or moves the cranial spacer paddle 512 with respect to the caudal spacer paddle 515 thereby adjusting the height of the interspinous spacer assembly 500. Once the interspinous spacer assembly 500 has been properly positioned, the assembly locking knob 596 is rotated, which in turn, rotates the set screw engaging device and hence the set screw disposed in the screw recess 581 to secure the position of the cranial spacer paddle 512 with respect to the caudal spacer paddle 515. Reverse rotation of the assembly holding knob 594 releases the tool 590 from the interspinous spacer assembly 500.

As illustrated and described in connection with FIG. 9, the width of the interspinous spacer assembly 500 is preferably nonadjustable. However, as will be appreciated by one of ordinary skill in the art, the width of the interspinous spacer assembly 500 of the fifth preferred embodiment may be adjustable by any means disclosed herein or known. In addition, the angulation of the cranial and caudal wings 530, 540, 545 may be adjusted by varying the location that wings 530, 540, 545 are fixed to the spinous processes SP. Alternatively, the cranial and caudal wings 530, 540, 545 may be separately and adjustably coupled to the cranial and caudal paddles 512, 515.

Figure 11A:
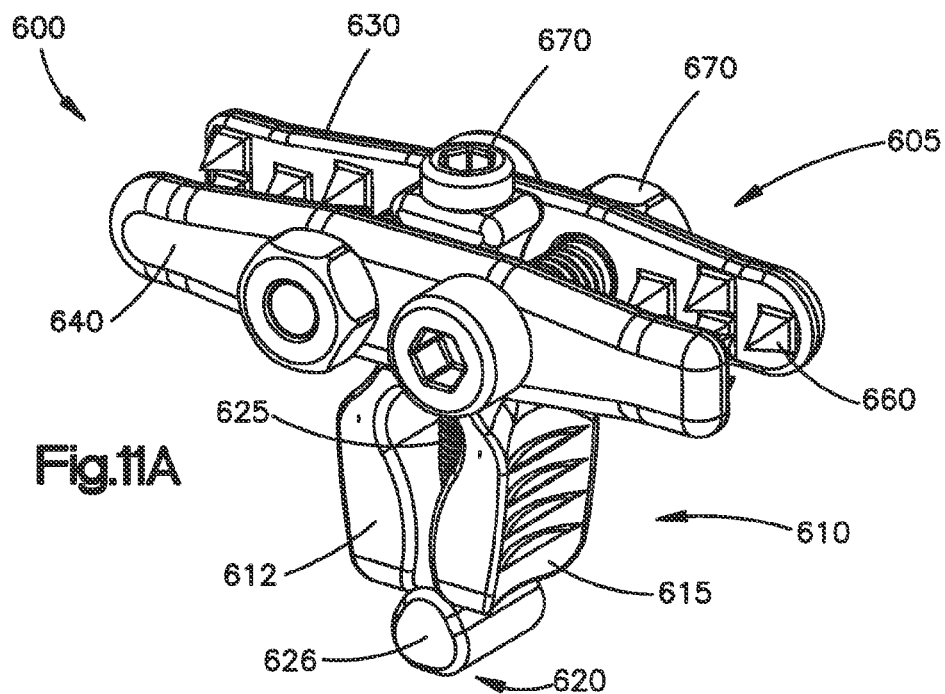
FIG. 11A illustrates a side perspective view of a sixth preferred embodiment of an interspinous spacer assembly in accordance with the present invention.
Figure 11B:
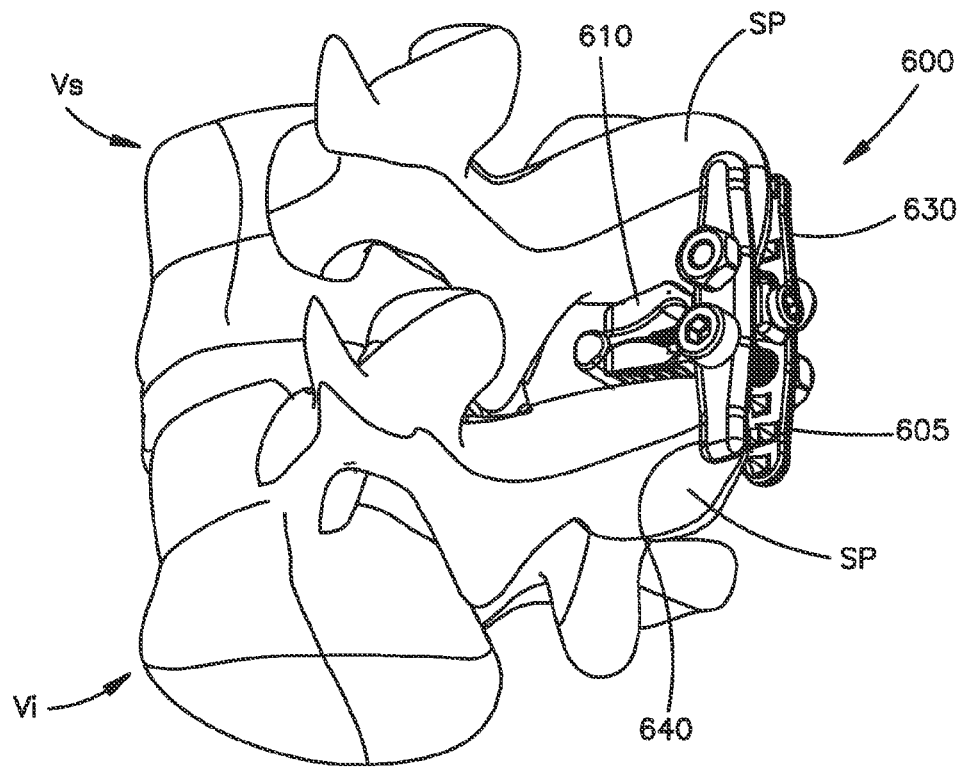
FIG. 11B illustrates a side perspective view of the interspinous spacer assembly shown in FIG. 11A coupled to adjacent spinous processes.

Referring to FIGS. 11A and 11B, a sixth preferred embodiment of an interspinous spacer assembly 600 includes an interspinous spacer member 610 and an engagement mechanism 605. In the sixth preferred embodiment, the engagement mechanism 605 includes lateral plates 630, 640. The lateral plates 630, 640 are preferably constructed such that the height of the interspinous spacer assembly 600 is non-adjustable. The interspinous spacer member 610 operates as a tension band between adjacent spinous processes SP by being fixed at the interface of the supra spinous ligament and the spinous processes SP, as shown in FIG. 11B, thus preserving the muscles attached to the spinous processes SP and enabling a relatively less invasive implantation procedure. Alternatively, as will be readily appreciated by one of ordinary skill in the art, the lateral plates 630, 640 may be replaced by adjustable height plates as described herein or known for such purposes.

The lateral plates 630, 640 are preferably coupled to one another by any means herein described or known for such purpose. In addition, the lateral plates 630, 640 may be coupled to the adjacent spinous processes SP by any means herein described or known for such purpose. For example, the lateral plates 630, 640 of the sixth preferred embodiment are coupled to one another by one or more threaded bolt and nut assemblies 670 and include a plurality of spikes 660 extending from an inner surface thereof so that, in use, rotation of the bolt and nut assemblies 670 compresses the lateral plates 630, 640 together and presses the spikes 660 into the spinous processes SP for securing the position of the interspinous spacer assembly 600.

The interspinous spacer member 610 of the sixth preferred embodiment includes a cranial paddle 612 for contacting an inferior surface of the superior spinous process SP, a caudal paddle 615 for contacting a superior surface of the inferior spinous process SP and a spreading element 620 for adjusting the height of the spacer member 610. The cranial and caudal paddles 612, 615 may be integrally formed with one another or they may be separately formed and operatively associated with one another. The cranial and caudal paddles 612, 615 may be operatively coupled to the plate portions 630, 640 by any means now or hereafter known. The spreading element 620 preferably includes a threaded shaft 625 and an enlarged head portion 626. In use, rotation of the threaded shaft 625 causes the enlarged end portion 626 to move towards the lateral plates 630, 640, thereby spreading the cranial and caudal paddles 612, 615 and adjusting the height and, preferably, the angle of the interspinous spacer member 610 of the sixth preferred embodiment. The interspinous spacer member 610 may be inserted through the supra spinous ligament or laterally into the interspinous space.

Referring to FIGS. 12A and 12B, a seventh preferred embodiment of the interspinous spacer assembly 700 includes a cranial spacer paddle 712 for contacting an inferior surface of the superior spinous process SP and a caudal spacer paddle 715 for contacting a superior surface of the inferior spinous process, the cranial spacer paddle 712 being moveable with respect to the caudal spacer paddle 715 so that the overall height of interspinous spacer member 710 can be adjusted. The bone contacting surfaces of the cranial and caudal paddles 712, 715 may include a plurality of ridges 725 for contacting the adjacent spinous processes SP. The ridges 725 may also be in the form of spikes or teeth. In addition, the bone contacting surface of the cranial paddle 712 may be curved while the bone contacting surface of the caudal paddle 715 may be flat or generally planar for optimally conforming to the natural curvature of the spinous processes SP.

The position of the cranial and caudal paddles 712, 715, and hence the height of the interspinous spacer member 710, may be adjusted by any mechanism herein described or known for such purpose. Preferably, the cranial paddle 712 is integrally formed with or coupled to wings 740, 745 and the caudal paddle 715 is integrally formed with or coupled to wings 730, 735, wherein the wings 740, 745, 730, 735 are telescopically associated with one another. As a result, because the cranial and caudal paddles 712, 715 of the interspinous spacer member 710 are integrated with the wings 730, 735, 740, 745, adjustment of the height of the interspinous spacer member 710 also adjusts the overall height of the interspinous spacer assembly 700.

In use, the wings 730, 735, 740, 745 are preferably configured as plate portions, more preferably bendable plate portions so that the wings 730, 735, 740, 745 can be adjusted to engage spinous processes SP of various thicknesses. The wings 730, 735, 740, 745 may be fixed to the spinous processes SP by any mechanism herein described or known for such purposes including screws, rivets, etc.

The cranial and caudal spacer paddles 712, 715 may be configured so that they interconnect when the height of the interspinous spacer member 710 is minimized. This may be achieved by including a recess 713 formed in the cranial paddle 712 for receiving a raised portion 716 formed on the caudal paddle 715.

Referring to FIGS. 13A-D, an eighth preferred embodiment of the interspinous spacer assembly 800 includes only an interspinous spacer member 810. The interspinous spacer member 810 preferably includes a cranial spacer portion 812 for contacting an inferior surface of the superior spinous process SP, a caudal spacer portion 815 for contacting a superior surface of the inferior spinous process SP, wherein the cranial spacer portion 812 is moveable with respect to the caudal spacer portion 815 so that the overall height of interspinous spacer member 810 can be adjusted. The bone contacting surfaces of the cranial and caudal portions 812, 815 may include a plurality of ridges 825 for contacting the adjacent spinous processes SP. The ridges 825 may also be in the form of spikes or teeth. In addition, the bone contacting surface of the cranial portion 812 may be curved while the bone contacting surface of the caudal portion 815 may be flat to adapt to the natural curvature of the spinous processes SP.

The interspinous spacer member 810 of the eighth preferred embodiment is adjustable from a non-expanded, collapsed configuration (as shown in FIG. 13A) to an expanded, deployed configuration (as shown in FIG. 13B). In addition, the interspinous spacer member 810 is preferably configured to be incrementally adjustable as well (as exemplary illustrated in FIG. 13C). The cranial spacer portion 812 and the caudal spacer portion 815 may be interconnected by any means described herein, or any means now known or later discovered for such purpose. Preferably, the cranial spacer portion 812 and the caudal spacer portion 815 are interconnected by a ratchet-type mechanism 830 on the anterior and posterior ends of the spacer member 810. For example, the caudal spacer portion 815 may include a plurality of teeth 816 for engaging one or more corresponding teeth 813 formed on the cranial spacer portion 812.

In use, the interspinous spacer member 810 may be adapted by the user to the patient's anatomy during implantation by adjusting the height of the spacer member 810. Moreover, as will be appreciated by one or ordinary skill in the art, the angulation of the spacer member 810 may be adjusted by independently adjusting the anterior and posterior ends of the spacer member 810.

Figure 14A:
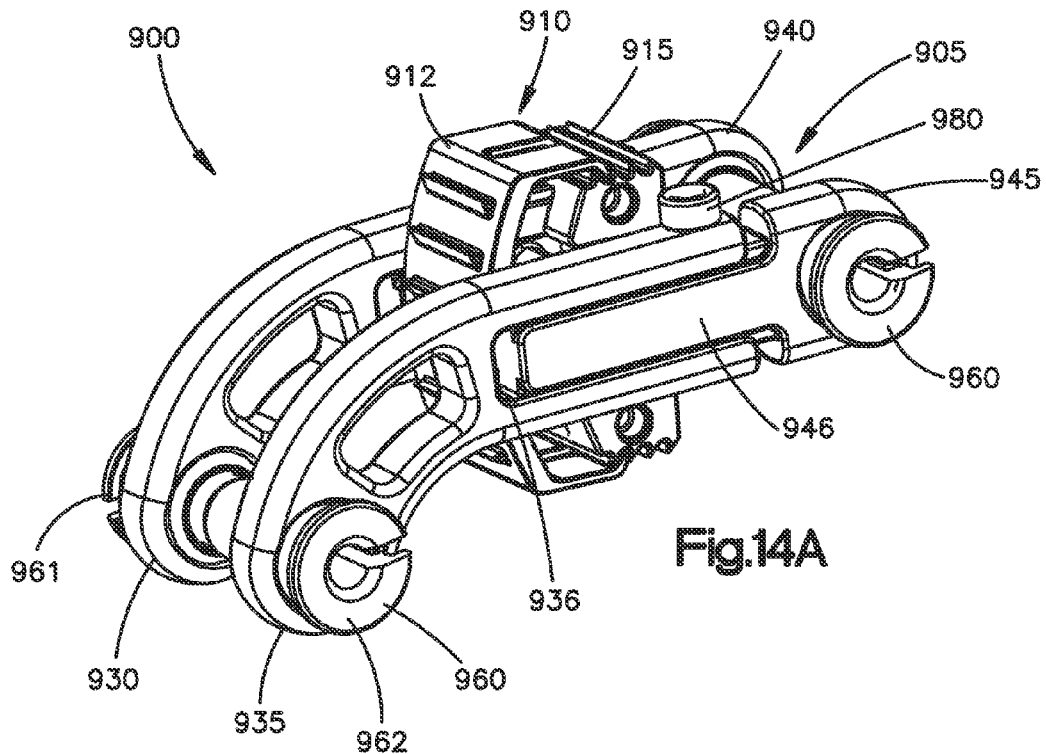
FIG. 14A illustrates a side perspective view of a ninth preferred embodiment of an interspinous spacer assembly according to the present invention, the interspinous spacer assembly including the interspinous spacer member shown in FIGS. 13A-13D with an adjustable engagement mechanism for adjustably coupling the spacer member to adjacent spinous processes.
Figure 14B:
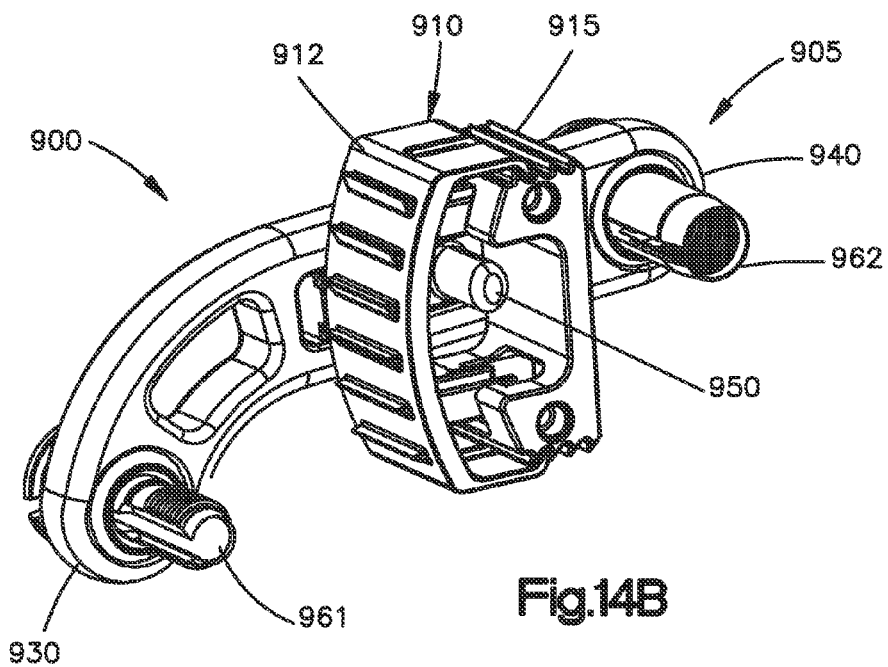
FIG. 14B illustrates a partial, side perspective view of the interspinous spacer assembly shown in FIG. 14A.
Figure 14C:
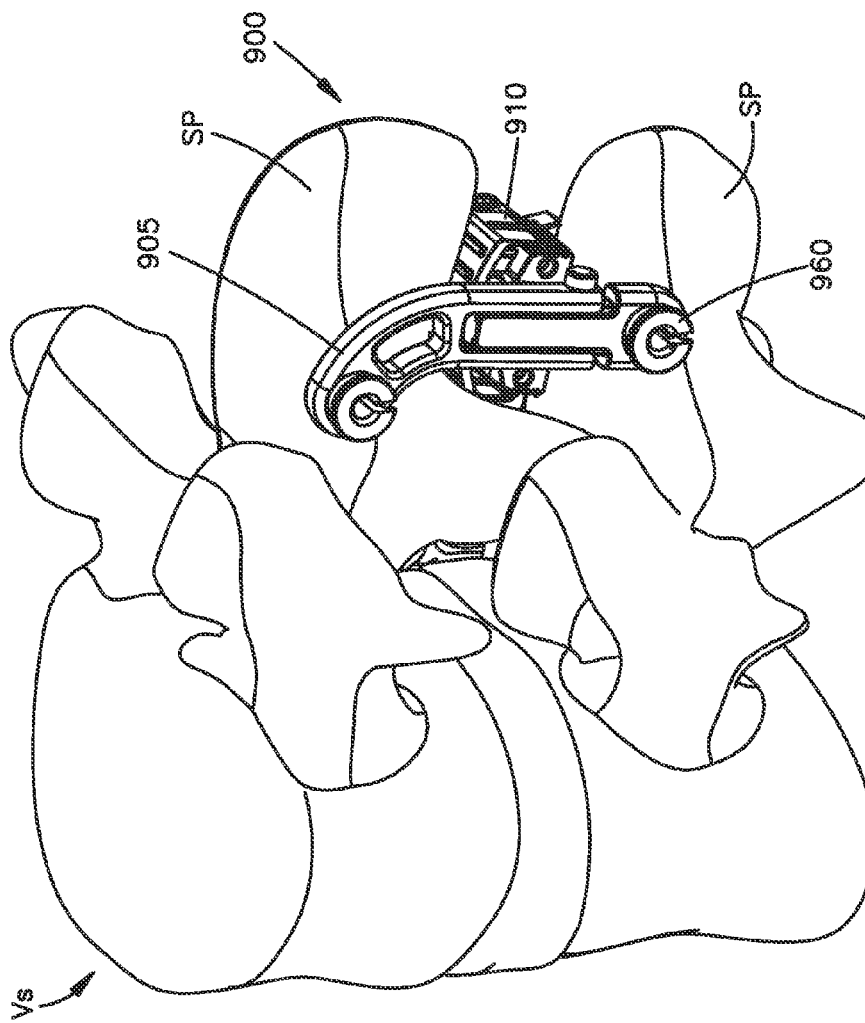
FIG. 14C illustrates a side perspective view of the interspinous spacer assembly shown in FIG. 14A coupled to adjacent spinous processes.
Figure 16A:
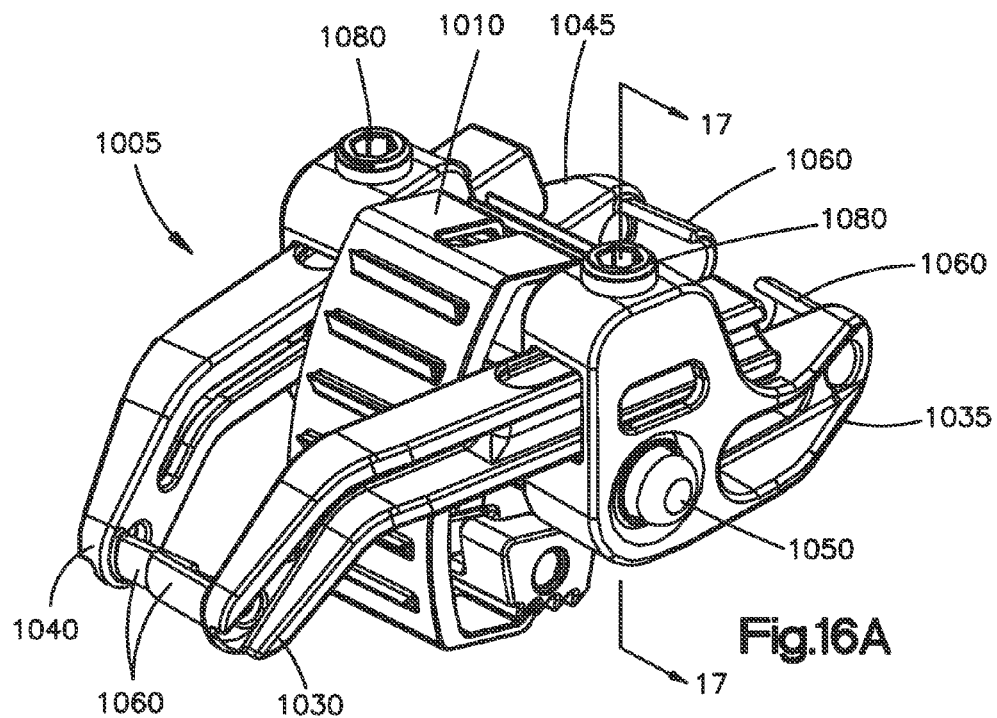
FIG. 16A illustrates a side perspective view of a tenth preferred embodiment of an interspinous spacer assembly according to the present invention, the interspinous spacer assembly including the interspinous spacer member shown in FIGS. 13A-13D with adjustable engagement mechanism for adjustably coupling the spacer member to adjacent spinous processes.
Figure 16B:
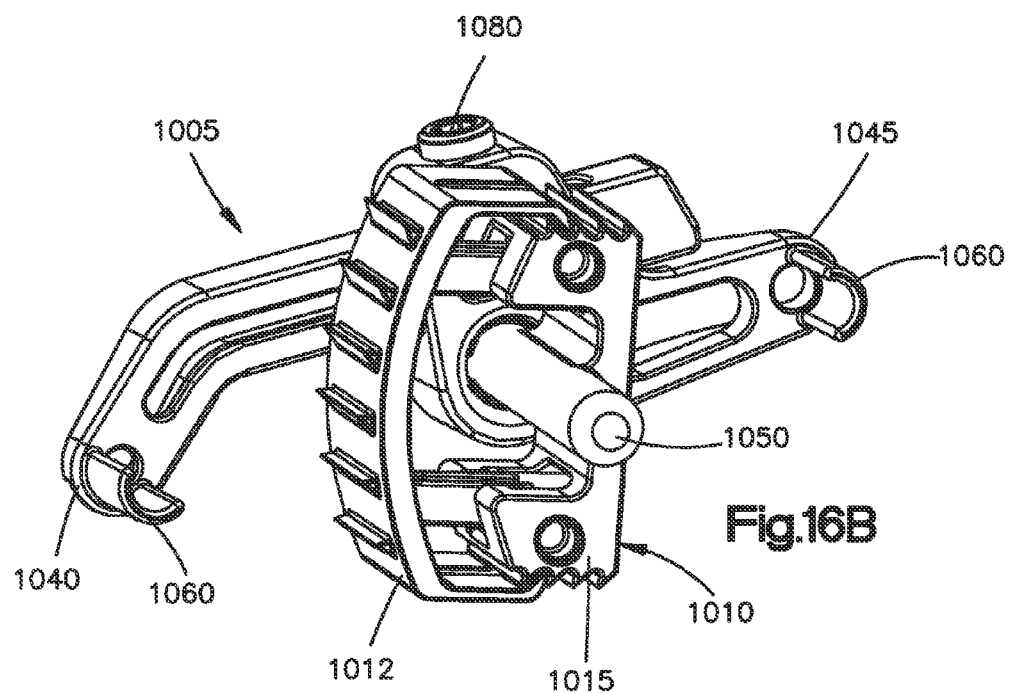
FIG. 16B illustrates a partial, side perspective view of the interspinous spacer assembly shown in FIG. 16A.
Figure 17:
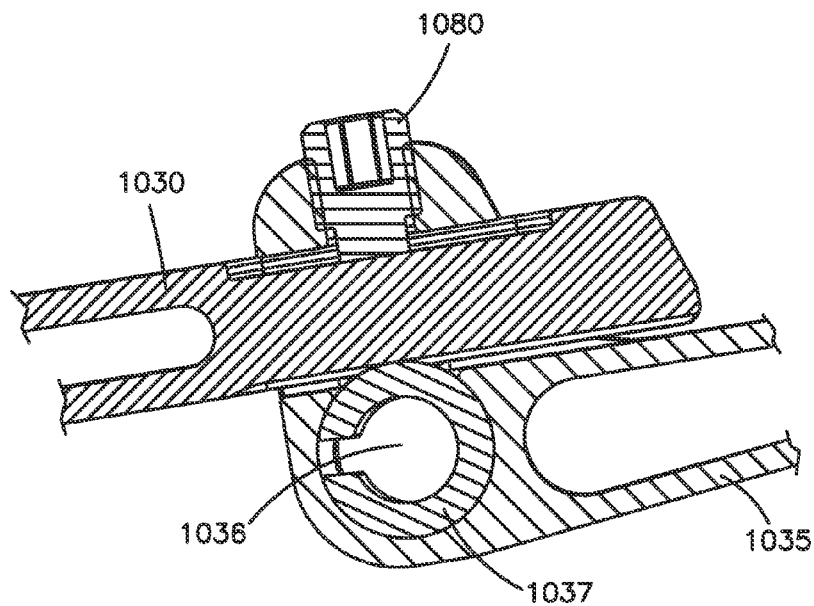
FIG. 17 is a cross-sectional view of the interspinous spacer assembly taken alone line 17-17 from FIG. 16A.

Referring to FIGS. 14A-C, a ninth preferred embodiment of the interspinous spacer assembly 900 is similar to the interspinous spacer member 810 of the eight preferred embodiment as described above in connection with FIGS. 13A-D. Thus, additional discussion of the interspinous spacer member 910 of the ninth preferred embodiment is omitted herein for the sake of brevity. In this ninth preferred embodiment, the interspinous spacer assembly 900 includes an engagement mechanism 905 for coupling the interspinous spacer member 910 to the adjacent spinous processes SP.

The engagement mechanism 905 preferably is in the form of telescopic plate portions 930, 935, 940, 945. That is, similar to previous embodiments discussed above, the engagement mechanism 905 may include first, second, third and fourth plate portions 930, 935, 940, 945 wherein the fourth plate portion 945 includes a male portion 946 slidably disposed within a female portion or recess 936 formed in the second plate portion 935 so that the fourth plate portion 945 is telescopingly received within the second plate portion 935 to form a first lateral plate. Similarly, the third plate portion 940 may include a male portion (not shown) slidably disposed within a female portion or recess (not shown) formed in the first plate portion 930 so that third plate portion 940 is telescopingly received within the first plate portion 930 to form a second lateral plate. However, it is envisioned that each plate portion 930, 935, 940, 945 may include more than one interlocking male and female portion. The position of the first and second lateral plates may be fixed by one or more set screws 980. As shown, the first and second plate portions 930, 935 may be curved to assist with securement to the adjacent spinous processes SP.

One or more of the plate portions 930, 935, 940, 945 of the ninth preferred embodiment includes a motion limiting element 950. As shown, the motion limiting element 950 may be in the form of a pin extending from an inner surface of one or more of the plate portions 930, 935, 940, 945. In use, the motion limiting element 950 passes through an interior space of the interspinous spacer member 910. The pin 950 limits the amount that the interspinous spacer member 910 can move posteriorly or anteriorly, but allows the interspinous spacer member 910 to otherwise float freely to enable better adaptation to the individual patient's anatomy. The interspinous spacer member 910 is preferably fixed laterally by the plate portions 930, 935, 940, 945.

Figure 15:
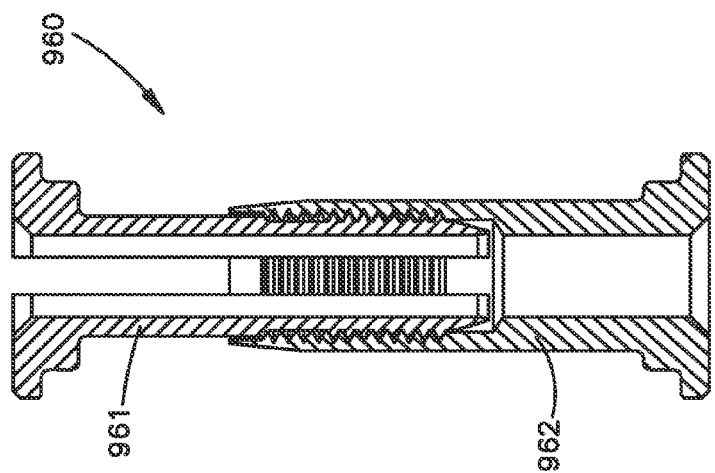
FIG. 15 illustrates a cross-sectional view of an exemplary linear ratchet mechanism for coupling the interspinous spacer assemblies to the adjacent spinous processes.

The engagement mechanism 905 (e.g., plate portions 930, 935, 940, 945) may be coupled to the adjacent spinous processes SP by any means described herein, or any means now known or later discovered for such purpose. Preferably, the engagement mechanism 905 (e.g., plate portions 930, 935, 940, 945) is coupled to the adjacent spinous processes SP by an interlocking linear ratchet mechanism 960, a cross-sectional view of which is shown in FIG. 15. Each interlocking linear ratchet mechanism 960 includes an externally toothed male portion 961 for ratchetably engaging an internally toothed female portion 962. Each of the toothed male and female portions 961, 962 preferably include a sharp, leading edge for cutting into the spinous processes SP during insertion. In use, the male portion 961 and the female portion 962 are inserted into the adjacent spinous processes SP from opposite lateral sides until the toothed portions of the male and female portions 961, 962 interlock with one another. Thereafter, the male and female portions 961, 962 may be compressed in a ratcheting manner to compress the engagement mechanism 905 (e.g., plate portions 930, 935, 940, 945) against the adjacent spinous processes SP. The male and female portions 961, 962 may be compressed by any mechanism now or hereafter known for such purpose. For example, a compression tool such as compression forceps, can be used to engage the interlocked male and female portions 961, 962. Actuation of the compression tool compresses the male and female portions 961, 962 and hence compresses the engagement mechanism 905 (e.g., plate portions 930, 935, 940, 945) against the adjacent spinous processes SP. Alternatively, the male and female portions 961, 962 may include corresponding threads so that the male and female portions 961, 962 may be threadably coupled to one another. Alternatively, the teeth formed on the male and female portions 961, 962 may be sized and configured to be either threadably coupled to one another or linearly actuated.

Referring to FIGS. 16A-18B, a tenth preferred embodiment of the interspinous spacer assembly 1000 includes an interspinous spacer member 1010 that is substantially the same as the interspinous spacer members 810, 910 of the eight and ninth preferred embodiments. Thus, additional discussion of the interspinous spacer member 1010 of the tenth preferred embodiments is omitted herein for the sake of brevity. In this tenth preferred embodiment, a motion limiting mechanism 1050 is in the form of a stabilization rod engaged to, for example, a caudal spacer portion 1015 for attaching the caudal spacer portion 1015 to an engagement mechanism 1005 while still allowing a cranial spacer portion 1012 to remain adjustable.

Similar to previous embodiments discussed above, the engagement mechanism 1005 preferably includes first, second, third and fourth telescopic members or plates 1030, 1035, 1040, 1045 including adjustable male and female portions so that the length of the engagement mechanism 1005 can be adjusted. The position and/or length of the engagement mechanism 1005 (i.e., telescopic members or plates 1030, 1035, 1040, 1045) may be secured via a compressive force via rotation of a set screw 1080. For example, referring to FIG.

17, the second telescopic member or plate 1035 may include a bore 1036 housing a compression nut 1037 for accepting one side of the stabilization rod 1050. Depending on the tightness of the set screw 1080, the compression nut 1037 will remain loose allowing the interspinous spacer member 1010 to rotate about an axis of the stabilization rod 1050 or the compression nut 1037 will become tightened to fix the position of the spacer member 1010.

Figures 18A, 18B:
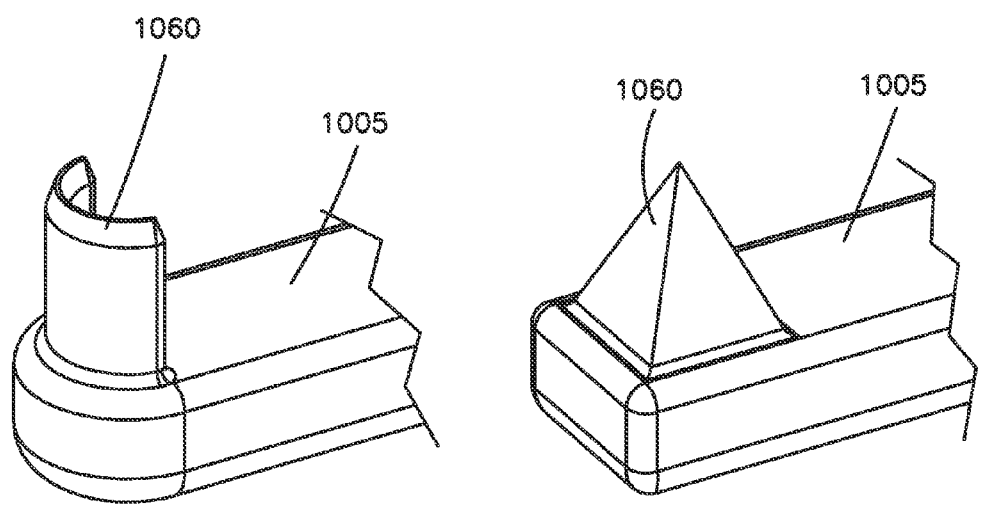
FIG. 18A illustrates a side perspective view of an exemplary spike for coupling the interspinous spacer assemblies to the adjacent spinous processes.
FIG. 18B illustrates an alternate, side perspective view of an exemplary spike for coupling the interspinous spacer assemblies to the adjacent spinous processes.

The engagement mechanism 1005 (i.e., telescopic members or plates 1030, 1035, 1040, 1045) may be coupled to the adjacent spinous processes SP by any means described herein, or any means now known or later discovered for such purpose. Preferably, as shown in FIGS. 18A and 18B, the engagement mechanism 1005 (i.e., telescopic members or plates 1030, 1035, 1040, 1045) may be attached to the spinous processes SP by one or more spikes 1060. The spikes 1060 may be of various shapes known in the art, but the spikes 1060 preferably include a semicircular shape (as shown in FIG. 18A) or a pyramid shape (as shown in FIG. 18B).

Referring to FIG. 19, an eleventh preferred embodiment of the interspinous spacer assembly 1100 includes an interspinous spacer member 1110 having a cranial spacer paddle 1112 for contacting an inferior surface of the superior spinous process SP and a caudal spacer paddle 1115 for contacting a superior surface of the inferior spinous process. The cranial spacer paddle 1112 is preferably moveable with respect to the caudal spacer paddle 1115 so that the overall height of interspinous spacer member 1110 can be adjusted. The engagement mechanism 1105 preferably includes first, second, third and fourth telescopic members or plates 1130, 1135, 1140, 1145, similar to previous embodiments described above.

Figure 19A:
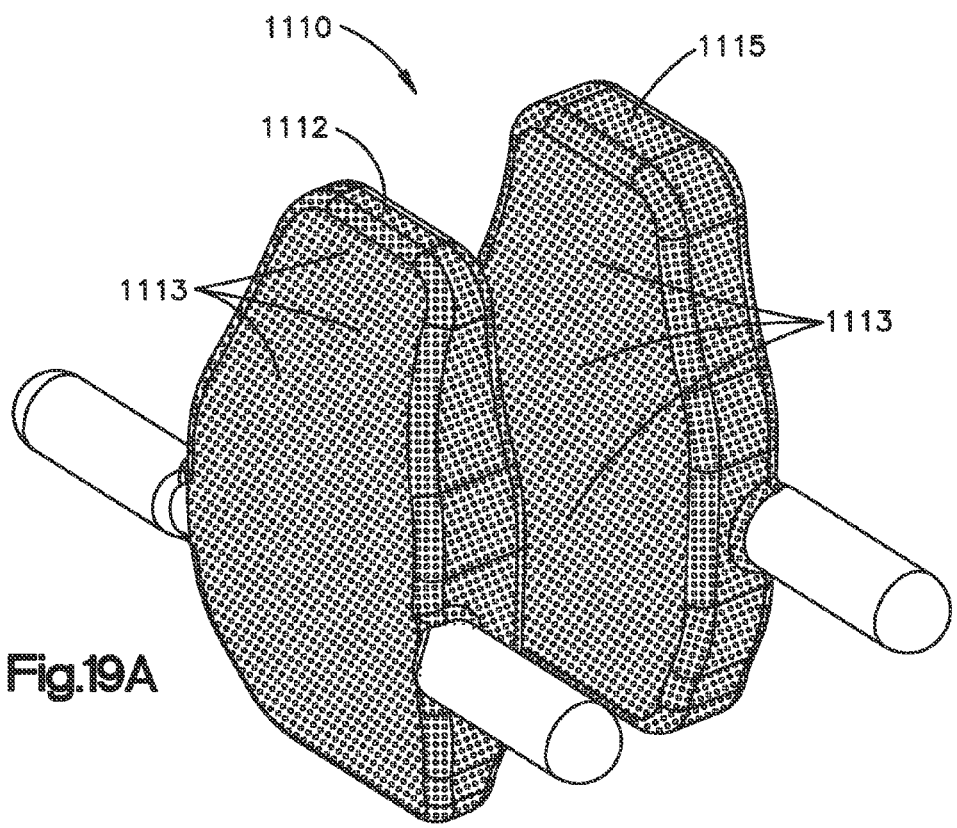
FIG. 19A illustrates a partial, side perspective view of the interspinous spacer assembly illustrated in FIG. 19 with the interspinous spacer member having pores.
Figure 19B:
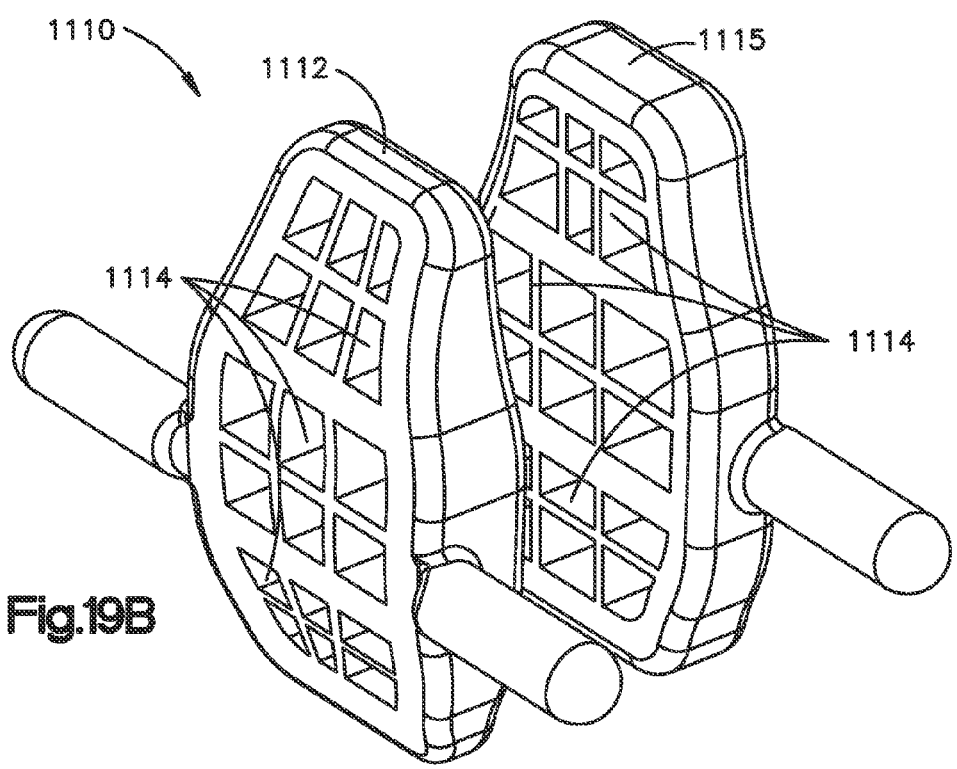
FIG. 19B illustrates a partial, side perspective view of the interspinous spacer assembly illustrated in FIG. 19 with the interspinous spacer member having cavities.

The interspinous spacer assembly 1100 of the eleventh preferred embodiment is depicted with its ventral (or anterior) side up to illustrate that the width of the cranial spacer paddle 1112 and the caudal spacer paddle 1115 tapered toward the ventral edge of the paddles 1112, 1115, wherein such tapered configuration aids implantation and may be used in any embodiment described herein. The bone contacting surface of the cranial spacer paddle 1112 may be curved for engaging the inferior surface of the superior spinous process SP while the bone contacting surface of the caudal paddle 1115 may be flat for adapting to the natural curvature of the spinal processes SP. Referring to FIG. 19A, the cranial spacer paddle 1112 and/or the caudal spacer paddle 1115 may include pores or perforations 1113. The pores or perforations 1113 may permit bone growth into the spacer paddles 1112, 1115. Referring to FIG. 19B, the cranial spacer paddle 1112 and/or the caudal spacer paddle 1115 may alternatively include cavities 1114. The cavities 1114 may permit bone growth and fusion through the spacer paddles 1112, 1115. The configurations of interspinous spacer member 1110 of the eleventh preferred embodiment with pores or perforations 1113 or with cavities 1114 may be applied to all the embodiments of the present invention, although it is not shown in the illustrative figures for other embodiments.

The cranial and caudal spacer paddles 1112, 1115 preferably include projections 1120, more preferably cylindrical projections, extending therefrom for engaging the engagement mechanism 1105 so that the orientation (e.g., angle) of the cranial and caudal spacer paddles 1112, 1115 can be adjusted. That is, by coupling the cranial and caudal spacer paddles 1112, 1115 to the engagement mechanism 1105 via cylindrical projections 1120, the cranial and caudal spacer paddles 1112, 1115 are allowed to rotate about their axes to thereby allow better adaptation of the interspinous spacer member 1110 within the interspinous space.

The cylindrical projections 1120 formed on the cranial and caudal spacer paddles 1112, 1115 are preferably received in bores 1125, preferably cylindrical bores, formed in the engagement mechanism 1105 (i.e., telescopic members or plates 1130, 1135, 1140, 1145).

Furthermore, by coupling the cranial and caudal spacer paddles 1112, 1115 to the engagement mechanism 1105, the height of the interspinous spacer member 1110 is adjusted via adjustment of the engagement mechanism 1105 (i.e., telescopic members or plates 1130, 1135, 1140, 1145). That is, similar to previous embodiments discussed above, by telescopically adjusting the length of the engagement mechanism 1105 (i.e., telescopic members or plates 1130, 1135, 1140, 1145), the user is able to simultaneously adjust the height of the spacer member 1110, which is coupled thereto.

The engagement mechanism 1105 (i.e., telescopic members or plates 1130, 1135, 1140, 1145) is preferably outfitted with a stopper to limit the maximum extension of the engagement mechanism 1105 (i.e., telescopic members or plates 1130, 1135, 1140, 1145) and to prevent disassembly of the interspinous spacer assembly 1100. The stopper may be achieved in any number of ways known to those in the art. For example, one or more of the members or plates may include a radiussed flange 1136.

The position of the first, second, third and fourth telescopic members or plates 1130, 1135, 1140, 1145 may be fixed by any mechanism known in the art including, for example, via a set screw. Preferably, the position of the first, second, third and fourth telescopic members or plates 1130, 1135, 1140, 1145 is fixed via a bolt assembly, including a bolt 1170, a nut 1171 and an optional spacer 1172. Tightening of the bolt assembly preferably fixes the position of the first, second, third and fourth telescopic members or plates 1130, 1135, 1140, 1145 and fixes the angle of the cranial and caudal paddles 1112, 1115.

The engagement mechanism 1105 (i.e., telescopic members or plates 1130, 1135, 1140, 1145) is preferably bendable so that it may be adapted to various spinous process thicknesses. One way of making the engagement mechanism 1105 (i.e., telescopic members or plates 1130, 1135, 1140, 1145) bendable is to taper or form a groove therein so that the telescopic members or plates 1130, 1135, 1140, 1145 bend at a pre-defined location.

The engagement mechanism 1105 (i.e., telescopic members or plates 1130, 1135, 1140, 1145) may be coupled to the adjacent spinous processes SP by any means described herein, or any means now known or later discovered for such purpose, including, for example, via rivets, screws or other fixation techniques. Preferably, the engagement mechanism 1105 (i.e., telescopic members or plates 1130, 1135, 1140, 1145) is fixed to the adjacent interspinous processes SP by of a bolt mechanism 1160, as previously described and illustrated in FIG. 15.

Referring to FIG. 20, one lateral side of a twelfth preferred embodiment of an interspinous spacer assembly 1200 includes a spacer member 1210 and an engagement mechanism 1205 that are similar to the spacer member 1110 and the engagement mechanism 1105 of the interspinous spacer assembly 1100 of the eleventh preferred embodiment. Thus, additional discussion of the interspinous spacer member 1210 and engagement mechanism 1205 of the twelfth preferred embodiment is omitted herein for the sake of brevity. In this twelfth preferred embodiment, the interspinous spacer assembly 1200 is constructed as a multilevel construct having a plurality of bores 1225 for receiving two or more interspinous spacer members 1210, each including cranial and caudal spacer paddles 1212, 1215, as described above. In addition, the engagement mechanism 1205 (i.e., telescopic members or plates 1230, 1235, 1240, 1245) is interconnected via one or more additional members so that the engagement mechanism 1205 (i.e., telescopic members or plates 1230, 1235, 1240, 1245) can span multiple levels and engage multiple interspinous spacer members 1210. As shown, telescopic members or plates 1230, 1245 are interconnected by first and second telescopic extension members 1280, 1290 forming a series of plate portions to create one lateral plate that is adjustable in length and capable of spanning multiple levels.

In use, the first telescopic extension member 1280 is telescopically coupled to the fourth plate 1245. Likewise the second telescopic extension member 1290 is telescopically coupled to the first plate 1230. Finally, the second telescopic extension member 1290 is telescopically received in the first extension member 1280. As will be readily appreciated by one of ordinary skill in the art, the interspinous spacer assembly 1200 of the twelfth preferred embodiment can include any number of extension members including, but not limited to, one, three, four or more. The interspinous spacer assembly 1200 may or may not be coupled to one or more intermediate spinous processes SP and the coupling may be accomplished by any means described herein, or any means now known or later discovered for such purpose.

Referring to FIGS. 21 and 22, a thirteenth preferred embodiment of the interspinous spacer assembly 1300 is constructed as a multi-level construct so that the interspinous spacer assembly 1300 can engage multiple levels, although a single level construct of the interspinous spacer assembly 1300 is also envisioned. The interspinous spacer assembly 1300 includes two interspinous spacer members 1310, each including a cranial spacer paddle 1312 for contacting an inferior surface of the superior spinous process SP and a caudal spacer paddle 1315 for contacting a superior surface of the inferior spinous process SP, wherein the cranial spacer paddle 1312 is moveable with respect to the caudal spacer paddle 1315 so that the overall height of interspinous spacer member 1310 can be adjusted. The bone contacting surfaces of the paddles 1312, 1315 may include a plurality of ridges 1325 for contacting the adjacent spinous processes SP. The ridges 1325 may also be spikes or teeth. In addition, the bone contacting surface of the cranial paddle 1312 may be curved while the bone contacting surface of the caudal paddle 1315 may be flat for conforming to the natural curvature of the spinous processes SP. It should be noted that the interspinous spacer assembly 1300 may include any number of interspinous spacer members 1310 including one, three, four or more.

The interspinous spacer assembly 1300 is shown with its ventral or anterior side up to illustrate that the width of the cranial and caudal spacer paddles 1312, 1315 may be tapered toward the ventral or anterior edge of the paddles 1312, 1315. This tapered configuration may be applied to all the embodiments of the present invention, although it is not shown in the illustrative figures for certain other embodiments.

The cranial and caudal paddles 1312, 1315 may be operatively coupled to the engagement mechanism 1305 by any means described herein, or known in the art for such purpose. Preferably the cranial and caudal paddles 1312, 1315 include cylindrical projections 1320 extending therefrom for being received within cylindrical bores or slots 1325 formed in the engagement mechanism 1305 so that the cranial and caudal paddles 1312, 1315 can rotate with respect to the engagement mechanism 1305 to better conform with the adjacent spinous processes SP.

In this thirteenth preferred embodiment, the engagement mechanism 1305 is preferably in the form of a plate assembly 1330 including integrated sliding plate assemblies 1350. That is, the engagement mechanism 1305 preferably includes first and second lateral plates 1330, 1340, wherein each lateral plate 1330, 1340 includes a recess formed therein for slidably receiving sliding plate assemblies 1350. The sliding plate assemblies 1350 are operatively coupled to at least one of the cranial and caudal spacer paddles 1312, 1315 so that movement of the sliding plate assemblies 1350 with respect to the lateral plates 1330, 1340 moves the cranial and/or caudal spacer members 1312, 1315 and hence adjusts the overall height of the interspinous spacer member 1310.

The sliding plate assemblies 1350 are preferably coupled to the lateral plate 1330, 1340 via a ratchet-type mechanism so that the position of the sliding plate assemblies 1350, and hence the position of the cranial and caudal spacer members 1312, 1315 can be incrementally adjusted, although it is envisioned that other coupling mechanism may be used including, for example, a tongue and groove type system. The sliding plate assemblies 1350 preferably include the bores and/or slots 1325 for accommodating the protrusions 1320 extending from the cranial and caudal spacer member 1312, 1315.

In use, the sliding plate assemblies 1350 are adjustable with respect to the lateral plate 1330, 1340 so that the position of the cranial spacer paddle 1312 and caudal spacer paddle 1315 can be adjusted relative to one another to thereby adjust the longitudinal location of the interspinous spacer member 1310 as well as the height of the interspinous spacer member 1310.

The engagement mechanism 1305 of the thirteenth preferred embodiment may be coupled to the adjacent spinous processes SP by any means described herein, or any means now known or later discovered for such purpose. Preferably, as shown, the engagement mechanism 1305 is coupled to the adjacent spinous processes SP via a bolting mechanism 1360 as previous described. The interspinous spacer assembly 1300 may or may not be coupled to one or more intermediate spinous processes SP and the coupling may be accomplished by any means described herein, or any means now known or later discovered for such purpose.

Referring to FIGS. 23A and 23B, a fourteenth preferred embodiment of the interspinous spacer assembly 1400 includes an interspinous spacer member 1410 having a cranial spacer part 1412 for contacting an inferior surface of a superior spinous process SP, a caudal spacer part 1415 for contacting a superior surface of an inferior spinous process SP, and an intermediate spacer part 1420 that is slidably disposed between the cranial spacer part 1412 and the caudal spacer part 1415. In use, multiple intermediate spacer parts 1420 of various heights may be provided to enable the user to select the appropriate size so that the overall height of the interspinous spacer member 1410 can be adjusted to suit the user's particular needs and the patient's specific anatomy.

The bone contacting surfaces of the cranial and caudal spacer parts 1412, 1415 may include a plurality of ridges 1425 for contacting the adjacent spinous processes SP. The ridges 1425 may also be spikes or teeth. In addition, the bone contacting surface of the cranial spacer part 1412 may be curved while the bone contacting surface of the caudal spacer part 1415 may be flat for conforming to the natural curvature of the spinal processes SP.

The cranial spacer part 1412, the caudal spacer part 1415 and the intermediate spacer part 1420 may be coupled together by any mechanism known in the art including, for example, bonding, welding, screw, rivet, thread, etc. Preferably, the cranial spacer part 1412 includes a recess (not shown) formed on an inner surface thereof for engaging a projection 1422 extending from an upper surface of the intermediate spacer part 1420, or vice versa. Similarly, the intermediate spacer part 1420 includes a recess 1424 formed on an inner surface thereof for engaging a projection 1417 extending from an upper surface of the caudal spacer part 1415, or vice versa.

The engagement mechanism 1405 of the interspinous spacer assembly 1400 of the fourteenth preferred embodiment is in the form of integral wings 1430, 1435, 1440, 1445 with one wing (shown as 1440) integrally formed with the cranial spacer part 1412, one wing (shown as wing 1430) integrally formed with the caudal spacer part 1415 and two wings (shown as 1435 and 1445) integrally formed with the intermediate spacer part 1420. However, as readily appreciated by one of ordinary skill in the art, the wings 1430, 1435, 1440, 1445 may be separated from and operatively coupled to the cranial spacer part 1412, caudal spacer part 1415 and intermediate spacer part 1420 by any mechanism described herein or known in the art for such purpose. Each of the wings 1430, 1435, 1440, 1445 may include a pad 1447 for contacting the spinous processes SP. The wings 1430, 1435, 1440, 1445 and/or pads 1447 can be fixed to the spinous processes SP by any mechanism described herein or known in the art for such purpose including but not limited to spikes, screws, rivets, bolts, etc.

In use, the interspinous spacer assembly 1400 is implanted by first implanting the cranial spacer part 1412 and the caudal spacer part 1415 in a collapsed configuration into the interspinous space from a first lateral side of the adjacent spinous processes SP and then distracted to the desired height. Once the desired distraction is achieved, the corresponding intermediate spacer part 1420 of a compatible height is inserted into the interspinous space and between the cranial spacer part 1412 and the caudal spacer part 1415 from a second lateral side of the adjacent spinous processes SP.

Figure 24C:
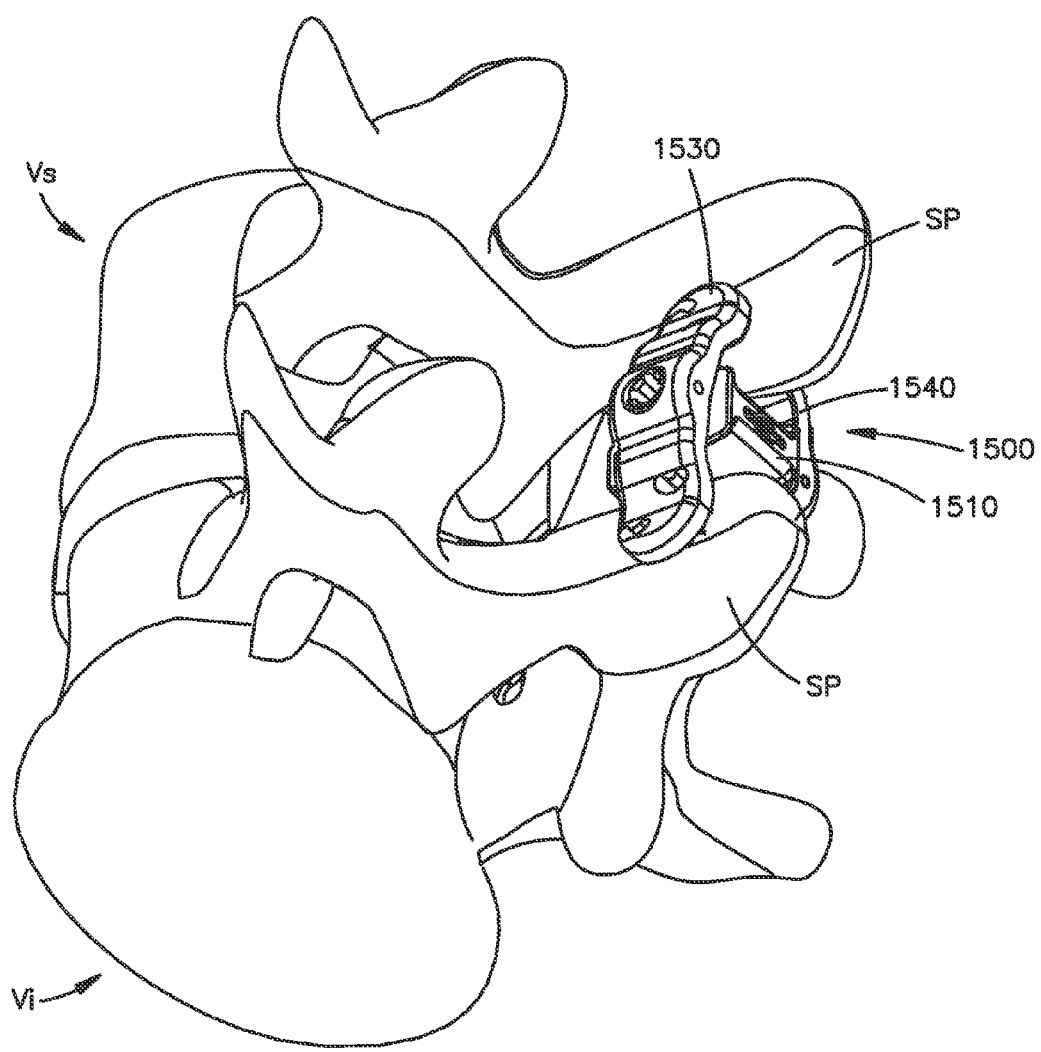
FIG. 24C illustrates a posterior perspective view of the interspinous spacer assembly shown in FIG. 24A coupled to adjacent spinous processes.

Referring to FIGS. 24A-C, a fifteenth preferred embodiment of the interspinous spacer assembly 1500 includes an interspinous spacer member 1510 and an engagement mechanism 1505 in the form of first and second lateral plates 1530, 1540. The interspinous spacer member 1510 is preferably in the form of a rigid, non-adjustable spacer member (i.e., fixed width and height spacer member), although other configurations including adjustable height spacer members as described herein are envisioned. The spacer member 1510 includes a cranial surface 1512 for contacting an inferior surface of the superior spinous process SP, a caudal surface 1515 for contacting a superior surface of the inferior spinous process SP, a ventral or anterior end 1517 and a dorsal or posterior end 1518. The ventral or anterior end 1517 preferably protrudes anteriorly beyond anterior edges of the lateral plates 1530, 1540 while the posterior or dorsal end 1518 preferably is flush with the posterior edges of the lateral plates 1530, 1540. The ventral or anterior end 1517 may also include a tapered width for facilitating insertion of the spacer member 1510 into the interspinous space. The posterior or dorsal end 1518 preferably includes a threaded borehole 1519 for threadably engaging a distal end of an insertion tool (not shown).

The interspinous spacer member 1510 may be coupled to the lateral plates 1530, 1540 by any mechanism described herein or known in the art for such purpose. Preferably, the interspinous spacer member 1510 includes a bore for receiving clips 1520 projecting from holes 1532 formed in the lateral plates 1530, 1540. Incorporation of the clips 1520 and holes 1532 preferably enables the interspinous spacer member 1510 to rotate and shift in any direction with respect to the lateral plates 1530, 1540 so that, in use, the interspinous spacer member 1510 can be rotated and shifted to adjust its angulation and position.

Once the interspinous spacer assembly 1500 has been properly positioned, the position of the spacer member 1510 can be fixed with respect to the lateral plates 1530, 1540 by, for example, inserting and rotating a tool in threaded borehole 1519 or rotating a set screw or other mechanism into engagement with the clips 1520. Alternatively, the spacer member 1510 may be left to rotate freely with respect to the lateral plates 1530, 1540.

The engagement mechanism 1505 (e.g., lateral plates 1530, 1540) may be coupled to the adjacent spinous processes SP by any mechanism described herein or known in the art for such purpose. Preferably, the engagement mechanism 1505 (e.g., lateral plates 1530, 1540) is coupled to the adjacent spinous processes SP by spikes 1560 extending from an inner surface thereof. More preferably, the spikes 1560 of the first lateral plate 1530 extend into and through the spinous processes SP so that they pierce the opposite lateral side of the spinous processes SP and the spikes 1560 are received within a corresponding hole 1561 formed in the second lateral plate 1540.

Referring to FIGS. 25A-D, a sixteenth preferred embodiment of the interspinous spacer assembly 1600 includes an interspinous spacer member 1610 having a non-adjustable, rigid spacer body, although other configurations are envisioned including adjustable height spacer members as described herein. The interspinous spacer member 1610 preferably includes a bore 1611 extending therethrough.

The engagement mechanism 1605 preferably is in the form of rotatable first, second, third and fourth wings 1630, 1635, 1640, 1645 extending from the spacer member 1610 for laterally engaging the spinous processes SP on both lateral sides of the spinous processes SP, preferably at the base of the spinous process SP (i.e., junction to lamina where bone is strongest). The first wing 1630 preferably includes a shaft 1670, more preferably a threaded shaft, extending perpendicularly therefrom, the shaft 1670 being sized and configured to pass through a bore 1611 formed in the interspinous spacer member 1610. The second, third and fourth wings 1635, 1640, 1645 preferably each include a bore 1636, 1641, 1646, respectively, for receiving the shaft 1670 so that the shaft 1670 extends through the bores 1636, 1641, 1646 formed in the second, third and fourth wings 1635, 1640, 1645 and the bore 1611 formed in the spacer member 1610.

More specifically, the interspinous spacer shaft 1670 is preferably integrated with the rotatable first wing 1630. The rotatable fourth wing 1645 preferably includes a cylindrically arranged vessel 1647 configured to slide over the interspinous spacer shaft 1670 and mate with a corresponding cylindrical vessel 1642 formed on the third rotatable wing 1640 to form a cylinder around the interspinous spacer shaft 1670. The cylinder formed by the vessels 1642, 1647 of the third and fourth rotatable wings 1640, 1645 are sized and configured to be slidably disposed within the bore 1611 formed in the spacer member 1610. The third rotatable wing 1635 is also placed on the interspinous spacer shaft 1670, which has threads to accommodate a fastening nut 1675, which preferably has grooves for accepting a tool to tighten the fastening nut 1675. In use, with the fastening nut 1675 in a loosened state, the first, second, third and fourth rotatable wings 1630, 1635, 1640, 1645 are fully rotatable so that they may be are properly positioned by the user on either side of the adjacent spinous processes SP. Once properly positioned, rotation of the fastening nut 1675 tightens the rotatable wings 1630, 1635, 1640, 1645 relative to one another.

The rotatable wings 1630, 1635, 1640, 1645 allow the interspinous spacer assembly 1600 to be introduced in a minimal invasive approach in a folded configuration as best shown in FIG. 25C. Thereafter, the user can deploy the wings 1630, 1635, 1640, 1645 by rotating them into proper position, after the interspinous spacer assembly 1600 has been positioned within the interspinous space between adjacent spinous processes SP.

Figure 26C:
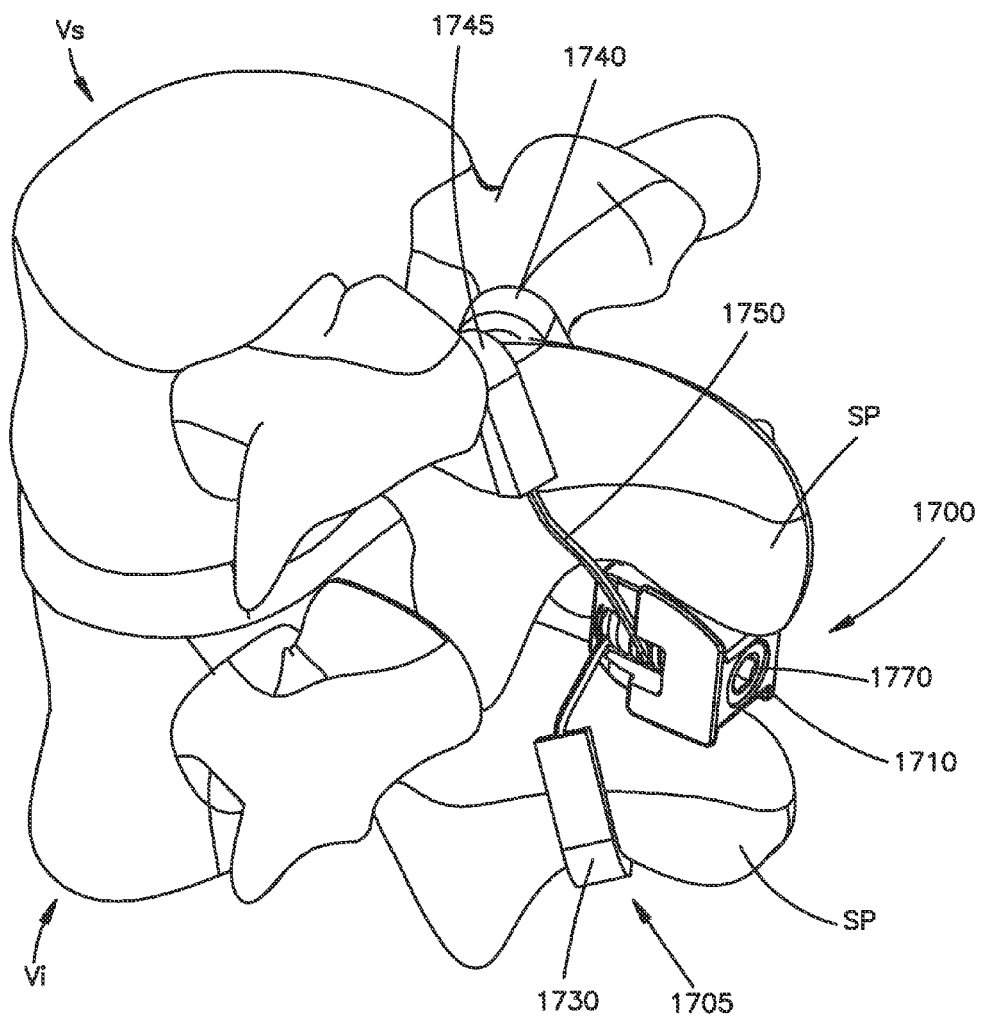
FIG. 26C illustrates a side perspective view of the interspinous spacer assembly of FIG. 26A coupled to adjacent spinous processes.

Referring to FIGS. 26A-C, a seventeenth preferred embodiment of the interspinous spacer assembly 1700 includes an interspinous spacer member 1710 and an engagement mechanism 1705. The interspinous spacer member 1710 is preferably constructed as a non-adjustable, rigid spacer member while the engagement mechanism 1705 is preferably in the form of a plurality of hooks 1730, 1735, 1740, 1745 connected to the interspinous spacer member 1710. Preferably, the hooks 1730, 1735, 1740, 1745 are connected to the spacer member 1710 via a cable 1750 so that the position of the hooks 1730, 1735, 1740, 1745 can be adjusted with respect to the spacer member 1710.

The interspinous spacer member 1710 preferably includes a hole 1711 extending therethrough for receiving a bolt 1770. The ends of the cables 1750 are spirally wound so that the ends of the cables 1750 can be received by, and preferably wrapped around reels 1771 that are operatively associated with bolt 1770. The interspinous spacer member 1710 may also include deploying holes 1722 for enabling the cables 1750 to pass therethrough. In use, rotation of the bolt 1770 in a first direction deploys the cables 1750 and the hooks 1730, 1735, 1740, 1745 with respect to the spacer member 1710 while rotation of the bolt 1770 in a second direction retracts the cables 1750, and the hooks 1730, 1735, 1740, 1745, with respect to the spacer member 1710.

In use, the cranial hooks 1730, 1735 are preferably attached to the cranial edge of the lamina of the cranial vertebra while the caudal hooks 1740, 1745 are preferably attached to the caudal edge of the lamina of the caudal vertebra, on either lateral side of the spinous processes SP, as best shown in FIG. 26C. After attachment of the lamina hooks 1730, 1735, 1740, 1745, rotation of the bolt 1770 retracts any slack in the cables 1750 thus tightening the cables 1750, fixing the position of the interspinous spacer member 1710, and applying compression to the spinal segments.

While the foregoing description and drawings represent preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. That is, features from one embodiment may be used in combination with or in place of features from another embodiment. The presently disclosed embodiments are therefore to be considered in all respects as illustrative and not restrictive, the scope of the invention being indicated by the appended claims, and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as described in the appended claims.

We claim:

1. An interspinous spacer assembly for insertion into an interspinous space between a spinous process of a superior vertebral body and a spinous process of an inferior vertebral body, the assembly comprising:
    an interspinous spacer member sized and configured for insertion into the interspinous space, the spacer member including a cranial surface for contacting an inferior surface of the spinous process of the superior vertebral body, a caudal surface for contacting a superior surface of the spinous process of the inferior vertebral body, a ventral end and a dorsal end that defines an threaded borehole, a set screw received within the threaded borehole, and a spacer bore extending through the interspinous spacer member; and
    an engagement mechanism that includes a first lateral plate and a second lateral plate for operatively coupling the spacer member to the spinous processes of the superior and inferior vertebral bodies, the first and second lateral plates each defining an interior surface that extends inward toward the interior surface of the opposing lateral plate, the engagement mechanism including a collapsible rod having a proximal end and a distal end each received within a plate bore provided in each of the first and second lateral plates, respectively, the proximal end connected to a first portion of the collapsible rod and the distal end connected to a second portion of the collapsible rod, the first portion and the second portion of the collapsible rod extending from the plate bore into the spacer bore, the proximal and distal ends of the collapsible rod not extending beyond an outside surface of the corresponding first and second lateral plates,
    wherein the first portion and the second portion of the collapsible rod are moveable relative to each other to narrow a distance between the first lateral plate and the second lateral plate to cause the first lateral plate and the second lateral plate to fix the engagement mechanism to the spinous processes,
    wherein the set screw fixes the position of the first portion and second portion of the collapsible rod, thereby fixing the position of the first lateral plate and the second lateral plate with respect to the interspinous spacer member;
    wherein the ventral end has a tapered width for facilitating insertion of the interspinous spacer member into the interspinous space, the tapered width defined by a left surface and opposing right surface each extending between the cranial and caudal surfaces.

2. The interspinous spacer assembly of claim 1, wherein the first portion and the second portion of the collapsible rod each include a frictional engagement portion to engage the first portion with the second portion.

3. The interspinous spacer assembly of claim 2, wherein a compression tool engages the first portion and the second portion to apply a substantially equal but opposite force on the first portion and the second portion, respectively, such that the first portion and the second are compressed together.

4. The interspinous spacer assembly of claim 2, wherein the frictional engagement portion is a toothed portion.

5. The interspinous spacer assembly of claim 1, wherein the engagement mechanism comprises spikes that extend from an inner surface of each of the first lateral plate or the second lateral plate, and wherein the spikes are adapted to extend into and through the spinous processes.

6. The interspinous spacer assembly of claim 5, wherein the spikes have a semicircular shape.

7. The interspinous spacer assembly of claim 5, wherein the spikes have a pyramid shape.

8. The interspinous spacer assembly of claim 5, wherein the spikes that extend from the inner surface of the first lateral plate engage a corresponding receiving hole in the second lateral plate, and wherein the spikes that extend from the second lateral plate engage a corresponding receiving hole in the first lateral plate.

9. The interspinous spacer assembly of claim 1, wherein the collapsible rod extends through the interspinous spacer member.

10. An interspinous spacer assembly for insertion into an interspinous space between a spinous process of a superior vertebral body and a spinous process of an inferior vertebral body, the assembly comprising:
an interspinous spacer member sized and configured for insertion into the interspinous space, the spacer member including a cranial surface for contacting an inferior surface of the spinous process of the superior vertebral body, a caudal surface for contacting a superior surface of the spinous process of the inferior vertebral body, a ventral end and a dorsal end, the dorsal end including a threaded borehole, a set screw received within the threaded borehole, and a spacer bore extending through the interspinous spacer member; and
an engagement mechanism that includes a first lateral plate and a second lateral plate for operatively coupling the spacer member to the spinous processes of the superior and inferior vertebral bodies, the first and second lateral plates each defining an interior surface that extends inward toward the interior surface of the opposing lateral plate, and a first clip and a second clip for operatively coupling the spacer member with the first and second lateral plates, the first clip and the second clip received within a plate bore extending through each of the first and second lateral plates, respectively, and into the spacer bore, the first clip and the second clip not extending beyond an outside surface of the corresponding first and second lateral plates, the engagement mechanism comprising spikes that extend from an inner surface of each of the first lateral plate or the second lateral plate, the spikes adapted to extend into and through the spinous processes to fix the engagement mechanism to the spinous processes,
wherein the set screw fixes the position of the first clip and the second clip, thereby fixing the position of the first lateral plate and the second lateral plate with respect to the interspinous spacer member;
wherein the ventral end has a tapered width for facilitating insertion of the interspinous spacer member into the interspinous space, the tapered width defined by a left surface and an opposing right surface each extending between the cranial and caudal surfaces.

11. The interspinous spacer assembly of claim 10, wherein interspinous spacer member is a rigid, non-adjustable spacer member having a fixed width and a fixed height.

12. The interspinous spacer assembly of claim 10, wherein the interspinous spacer member is rotatable about the first and second clip with respect to the engagement mechanism.

13. The interspinous spacer assembly of claim 12, wherein the interspinous spacer member is fixed with respect to the first lateral plate and the second lateral plate by the set screw inserted into the threaded borehole engaging the first and second clips.

14. The interspinous spacer assembly of claim 10, wherein the spikes have a semicircular shape.

15. The interspinous spacer assembly of claim 10, wherein the spikes have a pyramid shape.

16. The interspinous spacer assembly of claim 10, wherein the ventral end extends anteriorly beyond an anterior edge of the engagement mechanism and the dorsal end is substantially flushed with a posterior edge of the engagement mechanism.

17. The interspinous spacer assembly of claim 10, wherein the spikes that extend from the inner surface of the first lateral plate engage a corresponding receiving hole in the second lateral plate, and wherein the spikes that extend from the second lateral plate engage a corresponding receiving hole in the first lateral plate.

18. The interspinous spacer assembly of claim 10, wherein the spikes comprise a linear ratchet mechanism having a first toothed portion provided on the first lateral plate and a second toothed portion provided on the second lateral plate, and wherein the first toothed portion engages within the second toothed portion to fix the engagement mechanism to the spinous processes.

19. The interspinous spacer assembly of claim 18, wherein the linear ratchet mechanism comprises one of a bolt mechanism, rivets, threaded bolts and nuts and bone screws.

* * * * *